US012679900B2

(12) United States Patent
Chen et al.

(10) Patent No.: US 12,679,900 B2
(45) Date of Patent: Jul. 14, 2026

(54) ANTIBODIES BINDING RANKL AND USES THEREOF

(71) Applicant: BIOSION INC., Nanjing (CN)

(72) Inventors: Mingjiu Chen, Nanjing (CN); Cathy Xiaoyan Zhong, Nanjing (CN); Shukai Xia, Nanjing (CN)

(73) Assignee: BIOSION INC., Nanjing (CN)

( * ) Notice: Subject to any disclaimer, the term of this patent is extended or adjusted under 35 U.S.C. 154(b) by 960 days.

(21) Appl. No.: 17/783,346

(22) PCT Filed: Dec. 11, 2020

(86) PCT No.: PCT/CN2020/135970
§ 371 (c)(1),
(2) Date: Jun. 8, 2022

(87) PCT Pub. No.: WO2021/115465
PCT Pub. Date: Jun. 17, 2021

(65) Prior Publication Data
US 2023/0034768 A1 Feb. 2, 2023

Related U.S. Application Data

(60) Provisional application No. 62/947,541, filed on Dec. 13, 2019.

(51) Int. Cl.
*A61K 39/395* (2006.01)
*A61P 35/00* (2006.01)
*C07K 16/28* (2006.01)

(52) U.S. Cl.
CPC ...... *C07K 16/2875* (2013.01); *A61K 39/3955* (2013.01); *A61P 35/00* (2018.01);
(Continued)

(58) Field of Classification Search
None
See application file for complete search history.

(56) References Cited

U.S. PATENT DOCUMENTS 9,896,510 B2 * 2/2018 Zhou ....................... A61P 29/00

FOREIGN PATENT DOCUMENTS

CN 103060274 A 4/2013
EP 3085709 A1 10/2016
(Continued)

OTHER PUBLICATIONS

Prolia Highligts of Prescribing Information, Retrieved onine from: <ULR:https://www.accessdata.fda.gov/drugsatfda_docs/label/2019/125320s195lbl.pdf> [retrieved on Sep. 4, 2025], 32 pages, May 2019.*
(Continued)

*Primary Examiner* — Claire Kaufman
(74) *Attorney, Agent, or Firm* — Duane Morris LLP; Thomas J. Kowalski

(57) ABSTRACT

An isolated monoclonal antibody that specifically binds human RANKL, or the antigen-binding portion thereof. A nucleic acid molecule encoding the antibody or the antigen-binding portion thereof, an expression vector, a host cell and a method for expressing the antibody or the antigen-binding portion thereof are also provided. A treatment method using an anti-RANKL antibody or the antigen-binding portion is provided.

19 Claims, 11 Drawing Sheets
Specification includes a Sequence Listing.

| | chimeric B1A8 | chimeric D1A1 | chimeric B3D8 | chimeric D1E3 | denosumab |
|---|---|---|---|---|---|
| IC50 | 0.905 | 0.1115 | 3.166 | 0.05053 | 0.118 |

(52) U.S. Cl.
CPC .... *C07K 2317/24* (2013.01); *C07K 2317/565*
(2013.01); *C07K 2317/76* (2013.01)

(56) References Cited

FOREIGN PATENT DOCUMENTS

| WO | 2010134507 | A1 | 11/2010 |
| WO | 2012045481 | A2 | 4/2012 |
| WO | 2018223182 | A1 | 12/2018 |
| WO | 2019080909 | A1 | 5/2019 |

OTHER PUBLICATIONS

Sobacchi et al., The RANKL-RANK Axis: A Bone to Thymus
Round Trip, Front. Immunol. 10:629, 10 pages, Mar. 2019.*
Renema et al., RANK-RANKL signalling in cancer, Biosci. Rep.
36: e00366, 17 pages, 2016.*
Dougall, et al. Dual targeting of RANKL and PD-1 with a bispecific
antibody improves anti-tumor immunity, Clinical & Translational
Immunology (2019) vol. 8, e1081, p. 1-14.
International Search Report issued Mar. 10, 2021 in International
Application No. PCT/CN2020/135970.

* cited by examiner

| | mouse B1A8 | mouse B3D8 | denosumab |
|---|---|---|---|
| EC50 | 0.3965 | 0.1624 | 0.1283 |

| | mouse B4H5 | mouse D1A1 | mouse D1E3 | denosumab |
|---|---|---|---|---|
| EC50 | 0.5829 | 0.08256 | 0.04635 | 0.131 |

| | mouse B1A8 | mouse B3D8 | denosumab |
|---|---|---|---|
| IC50 | 0.2602 | 0.2328 | 0.1201 |

| | mouse B4H5 | mouse D1A1 | mouse D1E3 | denosumab |
|---|---|---|---|---|
| IC50 | 2.096 | 0.08024 | 0.03649 | 0.106 |

| | mouse B1A8 | mouse B3D8 | denosumab |
|---|---|---|---|
| IC50 | 0.498 | 0.5483 | 0.1107 |

| | mouse D1A1 | mouse D1E3 | denosumab |
|---|---|---|---|
| IC50 | 0.391 | 0.1642 | 0.1913 |

|  | denosumab | mouse B1A8 |
|---|---|---|
| IC50 | 0.6765 | 0.9667 |

|  | denosumab | mouse B3D8 | mouse D1A1 |
|---|---|---|---|
| IC50 | 0.4651 | 0.6255 | 0.839 |

| | denosumab | mouse D1E3 |
|---|---|---|
| IC50 | 0.6433 | 0.9978 |

| | denosumab | mouse B4H5 |
|---|---|---|
| IC50 | 0.3782 | 1.307 |

|  | denosumab | chimeric B1A8 | mouse B1A8 |
|---|---|---|---|
| EC50 | 0.3163 | 1.998 | 0.4928 |

|  | denosumab | chimeric B3D8 | mouse B3D8 |
|---|---|---|---|
| EC50 | 0.2164 | 3.165 | 0.4889 |

| | denosumab | chimeric D1E3 | mouse D1E3 |
|---|---|---|---|
| EC50 | 0.2693 | 0.1832 | 0.2464 |

| | denosumab | chimeric D1A1 | mouse D1A1 |
|---|---|---|---|
| EC50 | 0.3004 | 0.6242 | 1.114 |

| | chimeric B1A8 | chimeric D1A1 | chimeric B3D8 | chimeric D1E3 | denosumab |
|---|---|---|---|---|---|
| IC50 | 0.905 | 0.1115 | 3.166 | 0.05053 | 0.118 |

| | chimeric B1A8 | chimeric D1A1 | chimeric B3D8 | chimeric D1E3 | denosumab |
|---|---|---|---|---|---|
| IC50 | 4.4 | 0.4726 | 16.8 | 0.258 | 0.4552 |

| | mouse D1A1 | chimeric D1A1 | huD1A1-V2 | huD1A1-V5 | denosumab |
|---|---|---|---|---|---|
| EC50 | 0.6324 | 0.2573 | 0.2004 | 0.1825 | 0.153 |

| | mouse D1A1 | chimeric D1A1 | huD1A1-V2 | huD1A1-V5 | denosumab |
|---|---|---|---|---|---|
| IC50 | 0.4143 | 0.1548 | 0.154 | 0.1394 | 0.2266 |

| | mouse D1A1 | chimeric D1A1 | huD1A1-V2 | huD1A1-V5 | denosumab |
|---|---|---|---|---|---|
| IC50 | 1.278 | 0.4412 | 0.4444 | 0.338 | 0.4332 |

| | denosumab | huD1A1-V5 | huD1A1-V2 |
|---|---|---|---|
| IC50 | 0.9454 | ~ 1.424 | ~ 1.415 |

| | denosumab | mouse D1A1 | chimeric D1A1 |
|---|---|---|---|
| IC50 | 0.9244 | 3.414 | 1.392 |

| | chimeric D1A1 | huD1A1-V5 | huD1A1-V2 |
|---|---|---|---|
| IC50 | ~ 1.423 | 1.514 | ~ 1.445 |

SEQUENCE LISTING

```
<160> NUMBER OF SEQ ID NOS: 48

<210> SEQ ID NO 1
<211> LENGTH: 5
<212> TYPE: PRT
<213> ORGANISM: Artificial Sequence
<220> FEATURE:
<223> OTHER INFORMATION: VH CDR1 for mouse, chimeric and humanized D1A1

<400> SEQUENCE: 1

Asn Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: VH CDR1 for mouse and chimeric B1A8 and mouse
      and chimeric B3D8

<400> SEQUENCE: 2

Arg Tyr Gly Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: VH CDR1 for mouse and chimeric D1E3

<400> SEQUENCE: 3

Arg Tyr Ala Met Ser
1               5

<210> SEQ ID NO 4
<211> LENGTH: 6
<212> TYPE: PRT
<213> ORGANISM: Artificial Sequence
<220> FEATURE:
<223> OTHER INFORMATION: VH CDR1 for mouse B4H5

<400> SEQUENCE: 4

Ser Gly Tyr Ser Trp His
1               5

<210> SEQ ID NO 5
<211> LENGTH: 17
<212> TYPE: PRT
<213> ORGANISM: Artificial Sequence
<220> FEATURE:
<223> OTHER INFORMATION: VH CDR2 for mouse, chimeric and humanized D1A1

<400> SEQUENCE: 5

Gly Ile Ser Ser Gly Gly Thr Tyr Thr Tyr Tyr Pro Asp Thr Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: VH CDR2 for mouse and chimeric B1A8

<400> SEQUENCE: 6
```

```
Ser Ile Ser Ser Gly Gly Thr Tyr Thr Ser Tyr Pro Asp Ser Val Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: VH CDR2 for mouse and chimeric B3D8

<400> SEQUENCE: 7

Ser Ile Ser Ser Gly Gly Thr Tyr Thr Ser Tyr Pro Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: VH CDR2 for mouse and chimeric D1E3

<400> SEQUENCE: 8

Gly Ile Ser Ser Gly Gly Thr Tyr Thr Tyr Tyr Pro Asp Thr Val Lys
1               5                   10                  15

Gly

<210> SEQ ID NO 9
<211> LENGTH: 16
<212> TYPE: PRT
<213> ORGANISM: Artificial Sequence
<220> FEATURE:
<223> OTHER INFORMATION: VH CDR2 for mouse B4H5

<400> SEQUENCE: 9

Tyr Ile His Phe Ser Gly Ser Thr Asn Tyr Asn Pro Ser Leu Lys Ser
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: VH CDR3 for mouse, chimeric and humanized D1A1

<400> SEQUENCE: 10

Arg Asp Tyr Gly Asp Val Tyr Glu Trp Tyr Phe Asp Val
1               5                   10

<210> SEQ ID NO 11
<211> LENGTH: 14
<212> TYPE: PRT
<213> ORGANISM: Artificial Sequence
<220> FEATURE:
<223> OTHER INFORMATION: VH CDR3 for mouse and chimeric B1A8 and mouse
      and chimeric B3D8

<400> SEQUENCE: 11

Arg Asn Phe Ile Thr Ser Ala Thr Asp Cys Tyr Phe Asp Val
1               5                   10

<210> SEQ ID NO 12
<211> LENGTH: 13
```

```
<212> TYPE: PRT
<213> ORGANISM: Artificial Sequence
<220> FEATURE:
<223> OTHER INFORMATION: VH CDR3 for mouse and chimeric D1E3

<400> SEQUENCE: 12

Arg Asp Tyr Gly Asp Val Tyr Glu Trp Tyr Phe Asp Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: VH CDR3 for mouse B4H5

<400> SEQUENCE: 13

Ser Gly Pro Ser Thr Tyr Val Met Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: VL CDR1 for mouse, chimeric and humanized D1A1

<400> SEQUENCE: 14

Lys Ala Ser Gln Asp Val Arg Thr Ser Ile Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: VL CDR1 for mouse and chimeric B1A8 and mouse
        and chimeric B3D8

<400> SEQUENCE: 15

Arg Ala Ser Gln Ser Ile Ser Asn Asn Leu His
1               5                   10

<210> SEQ ID NO 16
<211> LENGTH: 11
<212> TYPE: PRT
<213> ORGANISM: Artificial Sequence
<220> FEATURE:
<223> OTHER INFORMATION: VL CDR1 for mouse and chimeric D1E3

<400> SEQUENCE: 16

Lys Ala Ser Gln Gly Val Arg Ile Ala Val Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: VL CDR1 for mouse B4H5

<400> SEQUENCE: 17

Lys Ala Ser Gln Asp Val Gly Ala Ala Val Gly
1               5                   10

<210> SEQ ID NO 18
<211> LENGTH: 7
```

```
<212> TYPE: PRT
<213> ORGANISM: Artificial Sequence
<220> FEATURE:
<223> OTHER INFORMATION: VL CDR2 for mouse, chimeric and humanized D1A1
      and mouse and chimeric D1E3

<400> SEQUENCE: 18

Ser Ala Ser Tyr Arg Tyr Thr
1               5

<210> SEQ ID NO 19
<211> LENGTH: 6
<212> TYPE: PRT
<213> ORGANISM: Artificial Sequence
<220> FEATURE:
<223> OTHER INFORMATION: VL CDR2 for mouse and chimeric B1A8 and mouse
      and chimeric B3D8

<400> SEQUENCE: 19

Ala Ser Gln Ser Ile Ser
1               5

<210> SEQ ID NO 20
<211> LENGTH: 7
<212> TYPE: PRT
<213> ORGANISM: Artificial Sequence
<220> FEATURE:
<223> OTHER INFORMATION: VL CDR2 for mouse B4H5

<400> SEQUENCE: 20

Trp Ala Ser Ile Arg Asp Thr
1               5

<210> SEQ ID NO 21
<211> LENGTH: 9
<212> TYPE: PRT
<213> ORGANISM: Artificial Sequence
<220> FEATURE:
<223> OTHER INFORMATION: VL CDR3 for mouse, chimeric and humanized D1A1

<400> SEQUENCE: 21

Gln Gln His Tyr Ser Ser Pro Trp Thr
1               5

<210> SEQ ID NO 22
<211> LENGTH: 9
<212> TYPE: PRT
<213> ORGANISM: Artificial Sequence
<220> FEATURE:
<223> OTHER INFORMATION: VL CDR3 for mouse and chimeric B1A8 and mouse
      and chimeric B3D8

<400> SEQUENCE: 22

Gln Gln Ser Asn Ser Trp Pro Phe Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL CDR3 for mouse and chimeric D1E3

<400> SEQUENCE: 23

Gln Gln His His Ser Ser Pro Trp Thr
1               5
```

<210> SEQ ID NO 24
<211> LENGTH: 9
<212> TYPE: PRT
<213> ORGANISM: Artificial Sequence
<220> FEATURE:
<223> OTHER INFORMATION: VL CDR3 for mouse B4H5

<400> SEQUENCE: 24

Gln His Tyr Asn Ser Tyr Pro Leu Thr
1               5

<210> SEQ ID NO 25
<211> LENGTH: 122
<212> TYPE: PRT
<213> ORGANISM: Artificial Sequence
<220> FEATURE:
<223> OTHER INFORMATION: VH for mouse and chimeric D1A1

<400> SEQUENCE: 25

Glu Val Gln Leu Val Glu Ser Gly Gly Gly Leu Val Lys Ser Gly Gly
1               5                   10                  15

Ser Leu Lys Leu Ser Cys Ala Ala Ser Gly Phe Thr Phe Arg Asn Tyr
            20                  25                  30

Ala Met Ser Trp Val Arg Gln Thr Pro Glu Lys Arg Leu Glu Trp Val
        35                  40                  45

Ala Gly Ile Ser Ser Gly Gly Thr Tyr Thr Tyr Tyr Pro Asp Thr Val
    50                  55                  60

Lys Gly Arg Phe Thr Ile Ser Arg Asp Asn Ala Arg Asn Thr Leu Phe
65                  70                  75                  80

Leu Gln Met Ser Ser Leu Arg Ser Glu Asp Thr Ala Met Tyr Tyr Cys
                85                  90                  95

Ala Arg Arg Asp Tyr Gly Asp Val Tyr Glu Trp Tyr Phe Asp Val Trp
            100                 105                 110

Gly Thr Gly Thr Thr Val Thr Val Ser Ser
        115                 120

<210> SEQ ID NO 26
<211> LENGTH: 122
<212> TYPE: PRT
<213> ORGANISM: Artificial Sequence
<220> FEATURE:
<223> OTHER INFORMATION: VH for D1A1-V1 to huB1H2-V6
<220> FEATURE:
<221> NAME/KEY: misc_feature
<222> LOCATION: (49)..(49)
<223> OTHER INFORMATION: Xaa can be Ala or Ser
<220> FEATURE:
<221> NAME/KEY: misc_feature
<222> LOCATION: (76)..(76)
<223> OTHER INFORMATION: Xaa can be Arg or Lys
<220> FEATURE:
<221> NAME/KEY: misc_feature
<222> LOCATION: (114)..(114)
<223> OTHER INFORMATION: Xaa can be Thr or Lys

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Xaa Gly Ile Ser Ser Gly Gly Thr Tyr Thr Tyr Tyr Pro Asp Thr Val
    50                  55                  60

```
Lys Gly Arg Phe Thr Ile Ser Arg Asp Asn Ala Xaa Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Asp Tyr Gly Asp Val Tyr Glu Trp Tyr Phe Asp Val Trp
            100                 105                 110

Gly Xaa Gly Thr Thr Val Thr Val Ser Ser
        115                 120
```

```
<210> SEQ ID NO 27
<211> LENGTH: 123
<212> TYPE: PRT
<213> ORGANISM: Artificial Sequence
<220> FEATURE:
<223> OTHER INFORMATION: VH for mouse and chimeric B1A8 and mouse and
      chimeric B3D8
<220> FEATURE:
<221> NAME/KEY: misc_feature
<222> LOCATION: (14)..(14)
<223> OTHER INFORMATION: Xaa can be Pro or Ser
<220> FEATURE:
<221> NAME/KEY: misc_feature
<222> LOCATION: (65)..(65)
<223> OTHER INFORMATION: Xaa can be Gln or Lys

<400> SEQUENCE: 27
```

```
Glu Val Gln Leu Val Glu Ser Gly Gly Asp Leu Val Lys Xaa Gly Gly
1               5                   10                  15

Ser Leu Lys Leu Ser Cys Ala Ala Ser Gly Phe Thr Phe Ser Arg Tyr
                20                  25                  30

Gly Met Ser Trp Val Arg Gln Thr Pro Asp Lys Arg Leu Glu Trp Val
            35                  40                  45

Ala Ser Ile Ser Ser Gly Gly Thr Tyr Thr Ser Tyr Pro Asp Ser Val
        50                  55                  60

Xaa Gly Arg Phe Thr Ile Thr Arg Asp Ser Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Asn Phe Ile Thr Ser Ala Thr Asp Cys Tyr Phe Asp Val
            100                 105                 110

Trp Gly Ala Gly Thr Thr Val Thr Val Ser Ser
        115                 120
```

```
<210> SEQ ID NO 28
<211> LENGTH: 122
<212> TYPE: PRT
<213> ORGANISM: Artificial Sequence
<220> FEATURE:
<223> OTHER INFORMATION: VH for mouse and chimeric D1E3

<400> SEQUENCE: 28
```

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
                20                  25                  30

Ala Met Ser Trp Val Arg Gln Thr Pro Glu Lys Arg Leu Glu Trp Val
            35                  40                  45

Ala Gly Ile Ser Ser Gly Gly Thr Tyr Thr Tyr Tyr Pro Asp Thr Val
        50                  55                  60

Lys Gly Arg Phe Thr Ile Ser Arg Asp Ser Ala Lys Asn Ile Leu Tyr
```

```
65                  70                  75                  80

Leu Gln Met Gly Ser Leu Arg Ser Glu Asp Ser Ala Met Tyr His Cys
                85                  90                  95

Ala Arg Arg Asp Tyr Gly Asp Val Tyr Glu Trp Tyr Phe Asp Val Trp
            100                 105                 110

Gly Thr Gly Thr Thr Val Thr Val Ser Ser
        115                 120

<210> SEQ ID NO 29
<211> LENGTH: 119
<212> TYPE: PRT
<213> ORGANISM: Artificial Sequence
<220> FEATURE:
<223> OTHER INFORMATION: VH for mouse B4H5

<400> SEQUENCE: 29

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Ser Ser Gly
            20                  25                  30

Tyr Ser Trp His Trp Ile Arg Gln Phe Pro Gly Asn Lys Leu Glu Trp
        35                  40                  45

Met Asp Tyr Ile His Phe Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Phe Ile Ser Val Thr Thr Glu Asp Thr Ala Thr Tyr Tyr Cys
                85                  90                  95

Ala Arg Ser Gly Pro Ser Thr Tyr Val Met Asp Tyr Trp Gly Gln Gly
            100                 105                 110

Thr Ser Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: VL for mouse and chimeric D1A1

<400> SEQUENCE: 30

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Ser
            20                  25                  30

Ile Ala Trp Tyr Gln Gln Lys Pro Gly Gln Ser Pro Asn Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Trp
                85                  90                  95

Thr Phe Gly Gly Gly Thr Lys Leu Glu Ile Lys
            100                 105

<210> SEQ ID NO 31
<211> LENGTH: 107
```

```
<212> TYPE: PRT
<213> ORGANISM: Artificial Sequence
<220> FEATURE:
<223> OTHER INFORMATION: VL for hu D1A1-V1 to hu D1A1-V6
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Ser
            20                  25                  30

Ile Ala Trp Tyr Gln Gln Lys Pro Gly Lys Xaa Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Xaa Ala Thr Tyr Tyr Cys Gln Gln His Tyr Ser Ser Pro Trp
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: VL for mouse and chimeric B1A8 and mouse and
      chimeric B3D8

<400> SEQUENCE: 32

Asp Thr Val Leu Thr Gln Ser Pro Ala Thr Leu Ser Val Thr Pro Gly
1               5                   10                  15

Ala Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Ile Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Ser Trp Pro Phe
                85                  90                  95

Thr Phe Gly Gly Gly Thr Lys Leu Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: VL for mouse and chimeric D1E3

<400> SEQUENCE: 33

Asp Ile Val Met Thr Gln Ser His Lys Phe Met Ser Ala Ser Val Gly
```

-continued

```
1               5                    10                   15
```

Asp Arg Val Ser Ile Thr Cys Lys Ala Ser Gln Gly Val Arg Ile Ala
            20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
            50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His His Ser Ser Pro Trp
            85                  90                  95

Thr Phe Gly Gly Gly Thr Lys Leu Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: VL for mouse B4H5

<400> SEQUENCE: 34

Asp Ile Val Met Thr Gln Ser His Arg Phe Met Ser Thr Ser Val Gly
1               5                    10                   15

Asp Arg Val Ser Ile Thr Cys Lys Ala Ser Gln Asp Val Gly Ala Ala
            20                  25                  30

Val Gly Trp Tyr Gln Gln Lys Pro Gly Gln Ser Pro Lys Leu Leu Ile
            35                  40                  45

Tyr Trp Ala Ser Ile Arg Asp Thr Gly Val Pro Asp Arg Phe Thr Gly
            50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln His Tyr Asn Ser Tyr Pro Leu
            85                  90                  95

Thr Phe Gly Gly Gly Thr Lys Leu Glu Ile Lys
            100                 105

<210> SEQ ID NO 35
<211> LENGTH: 326
<212> TYPE: PRT
<213> ORGANISM: Artificial Sequence
<220> FEATURE:
<223> OTHER INFORMATION: Heavy chain constant region for chimeric
     antibodies

<400> SEQUENCE: 35

Ala Ser Thr Lys Gly Pro Ser Val Phe Pro Leu Ala Pro Cys Ser Arg
1               5                    10                   15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95
```

-continued

```
Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
    130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175

Ser Thr Phe Arg Val Val Ser Val Leu Thr Val Val His Gln Asp Trp
            180             185             190

Leu Asn Gly Lys Glu Tyr Lys Cys Lys Val Ser Asn Lys Gly Leu Pro
            195             200             205

Ala Pro Ile Glu Lys Thr Ile Ser Lys Thr Lys Gly Gln Pro Arg Glu
    210             215             220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
            245             250             255

Ala Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
    290             295             300

Ser Val Met His Glu Ala Leu His Asn His Tyr Thr Gln Lys Ser Leu
305             310             315             320

Ser Leu Ser Pro Gly Lys
                325

<210> SEQ ID NO 36
<211> LENGTH: 327
<212> TYPE: PRT
<213> ORGANISM: Artificial Sequence
<220> FEATURE:
<223> OTHER INFORMATION: Heavy chain constant region for humanized
      antibodies

<400> SEQUENCE: 36

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
                85              90              95

Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
```

```
              115               120               125
Asp Thr Leu Met Ile Ser Arg Thr Pro Glu Val Thr Cys Val Val Val
    130               135               140

Asp Val Ser Gln Glu Asp Pro Glu Val Gln Phe Asn Trp Tyr Val Asp
145               150               155               160

Gly Val Glu Val His Asn Ala Lys Thr Lys Pro Arg Glu Glu Gln Phe
              165               170               175

Asn Ser Thr Tyr Arg Val Val Ser Val Leu Thr Val Leu His Gln Asp
              180               185               190

Trp Leu Asn Gly Lys Glu Tyr Lys Cys Lys Val Ser Asn Lys Gly Leu
              195               200               205

Pro Ser Ser Ile Glu Lys Thr Ile Ser Lys Ala Lys Gly Gln Pro Arg
    210               215               220

Glu Pro Gln Val Tyr Thr Leu Pro Pro Ser Gln Glu Glu Met Thr Lys
225               230               235               240

Asn Gln Val Ser Leu Thr Cys Leu Val Lys Gly Phe Tyr Pro Ser Asp
              245               250               255

Ile Ala Val Glu Trp Glu Ser Asn Gly Gln Pro Glu Asn Asn Tyr Lys
              260               265               270

Thr Thr Pro Pro Val Leu Asp Ser Asp Gly Ser Phe Phe Leu Tyr Ser
              275               280               285

Arg Leu Thr Val Asp Lys Ser Arg Trp Gln Gln Gly Asn Val Phe Ser
    290               295               300

Cys Ser Val Met His Glu Ala Leu His Asn His Tyr Thr Gln Lys Ser
305               310               315               320

Leu Ser Leu Ser Leu Gly Lys
              325

<210> SEQ ID NO 37
<211> LENGTH: 107
<212> TYPE: PRT
<213> ORGANISM: Artificial Sequence
<220> FEATURE:
<223> OTHER INFORMATION: Light chain constant region for chimeric and
      humanized antibodies

<400> SEQUENCE: 37

Arg Thr Val Ala Ala Pro Ser Val Phe Ile Phe Pro Pro Ser Asp Glu
1               5               10               15

Gln Leu Lys Ser Gly Thr Ala Ser Val Val Cys Leu Leu Asn Asn Phe
              20               25               30

Tyr Pro Arg Glu Ala Lys Val Gln Trp Lys Val Asp Asn Ala Leu Gln
              35               40               45

Ser Gly Asn Ser Gln Glu Ser Val Thr Glu Gln Asp Ser Lys Asp Ser
    50               55               60

Thr Tyr Ser Leu Ser Ser Thr Leu Thr Leu Ser Lys Ala Asp Tyr Glu
65               70               75               80

Lys His Lys Val Tyr Ala Cys Glu Val Thr His Gln Gly Leu Ser Ser
              85               90               95

Pro Val Thr Lys Ser Phe Asn Arg Gly Glu Cys
              100               105

<210> SEQ ID NO 38
<211> LENGTH: 452
<212> TYPE: PRT
<213> ORGANISM: Artificial Sequence
<220> FEATURE:
```

-continued

<223> OTHER INFORMATION: Heavy chain of denosumab

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly Lys
    450
```

```
<210> SEQ ID NO 39
<211> LENGTH: 215
<212> TYPE: PRT
<213> ORGANISM: Artificial Sequence
<220> FEATURE:
<223> OTHER INFORMATION: Light chain of denosumab

<400> SEQUENCE: 39

Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Ser Val Arg Gly Arg
            20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Phe Tyr Cys Gln Gln Tyr Gly Ser Ser Pro
            85              90              95

Arg Thr Phe Gly Gln Gly Thr Lys Val Glu Ile Lys Arg Thr Val Ala
            100             105             110

Ala Pro Ser Val Phe Ile Phe Pro Pro Ser Asp Glu Gln Leu Lys Ser
            115             120             125

Gly Thr Ala Ser Val Val Cys Leu Leu Asn Asn Phe Tyr Pro Arg Glu
            130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
            165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
            195             200             205

Ser Phe Asn Arg Gly Glu Cys
    210             215
```

```
<210> SEQ ID NO 40
<211> LENGTH: 414
<212> TYPE: PRT
<213> ORGANISM: Artificial Sequence
<220> FEATURE:
<223> OTHER INFORMATION: Human RANKL-Fc

<400> SEQUENCE: 40

Glu Pro Lys Ser Cys Asp Lys Thr His Thr Cys Pro Pro Cys Pro Ala
1               5               10              15

Pro Glu Leu Leu Gly Gly Pro Ser Val Phe Leu Phe Pro Pro Lys Pro
            20              25              30
```

-continued

```
Lys Asp Thr Leu Met Ile Ser Arg Thr Pro Glu Val Thr Cys Val Val
    35              40              45

Val Asp Val Ser His Glu Asp Pro Glu Val Lys Phe Asn Trp Tyr Val
    50              55              60

Asp Gly Val Glu Val His Asn Ala Lys Thr Lys Pro Arg Glu Glu Gln
65              70              75              80

Tyr Asn Ser Thr Tyr Arg Val Val Ser Val Leu Thr Val Leu His Gln
                85              90              95

Asp Trp Leu Asn Gly Lys Glu Tyr Lys Cys Lys Val Ser Asn Lys Ala
            100             105             110

Leu Pro Ala Pro Ile Glu Lys Thr Ile Ser Lys Ala Lys Gly Gln Pro
            115             120             125

Arg Glu Pro Gln Val Tyr Thr Leu Pro Pro Ser Arg Glu Glu Met Thr
    130             135             140

Lys Asn Gln Val Ser Leu Thr Cys Leu Val Lys Gly Phe Tyr Pro Ser
145             150             155             160

Asp Ile Ala Val Glu Trp Glu Ser Asn Gly Gln Pro Glu Asn Asn Tyr
                165             170             175

Lys Thr Thr Pro Pro Val Leu Asp Ser Asp Gly Ser Phe Phe Leu Tyr
            180             185             190

Ser Lys Leu Thr Val Asp Lys Ser Arg Trp Gln Gln Gly Asn Val Phe
            195             200             205

Ser Cys Ser Val Met His Glu Ala Leu His Asn His Tyr Thr Gln Lys
    210             215             220

Ser Leu Ser Leu Ser Pro Gly Lys Gly Ser Gln His Ile Arg Ala Glu
225             230             235             240

Lys Ala Met Val Asp Gly Ser Trp Leu Asp Leu Ala Lys Arg Ser Lys
                245             250             255

Leu Glu Ala Gln Pro Phe Ala His Leu Thr Ile Asn Ala Thr Asp Ile
            260             265             270

Pro Ser Gly Ser His Lys Val Ser Leu Ser Ser Trp Tyr His Asp Arg
            275             280             285

Gly Trp Gly Lys Ile Ser Asn Met Thr Phe Ser Asn Gly Lys Leu Ile
    290             295             300

Val Asn Gln Asp Gly Phe Tyr Tyr Leu Tyr Ala Asn Ile Cys Phe Arg
305             310             315             320

His His Glu Thr Ser Gly Asp Leu Ala Thr Glu Tyr Leu Gln Leu Met
                325             330             335

Val Tyr Val Thr Lys Thr Ser Ile Lys Ile Pro Ser Ser His Thr Leu
            340             345             350

Met Lys Gly Gly Ser Thr Lys Tyr Trp Ser Gly Asn Ser Glu Phe His
            355             360             365

Phe Tyr Ser Ile Asn Val Gly Gly Phe Phe Lys Leu Arg Ser Gly Glu
    370             375             380

Glu Ile Ser Ile Glu Val Ser Asn Pro Ser Leu Leu Asp Pro Asp Gln
385             390             395             400

Asp Ala Thr Tyr Phe Gly Ala Phe Lys Val Arg Asp Ile Asp
            405             410
```

<210> SEQ ID NO 41
<211> LENGTH: 415
<212> TYPE: PRT
<213> ORGANISM: Artificial Sequence
<220> FEATURE:

<223> OTHER INFORMATION: human RANK-Fc

<400> SEQUENCE: 41

Ile Ala Pro Pro Cys Thr Ser Glu Lys His Tyr Glu His Leu Gly Arg
1               5                   10                  15

Cys Cys Asn Lys Cys Glu Pro Gly Lys Tyr Met Ser Ser Lys Cys Thr
            20                  25                  30

Thr Thr Ser Asp Ser Val Cys Leu Pro Cys Gly Pro Asp Glu Tyr Leu
        35                  40                  45

Asp Ser Trp Asn Glu Glu Asp Lys Cys Leu Leu His Lys Val Cys Asp
    50                  55                  60

Thr Gly Lys Ala Leu Val Ala Val Val Ala Gly Asn Ser Thr Thr Pro
65                  70                  75                  80

Arg Arg Cys Ala Cys Thr Ala Gly Tyr His Trp Ser Gln Asp Cys Glu
                85                  90                  95

Cys Cys Arg Arg Asn Thr Glu Cys Ala Pro Gly Leu Gly Ala Gln His
            100                 105                 110

Pro Leu Gln Leu Asn Lys Asp Thr Val Cys Lys Pro Cys Leu Ala Gly
        115                 120                 125

Tyr Phe Ser Asp Ala Phe Ser Ser Thr Asp Lys Cys Arg Pro Trp Thr
    130                 135                 140

Asn Cys Thr Phe Leu Gly Lys Arg Val Glu His His Gly Thr Glu Lys
145                 150                 155                 160

Ser Asp Ala Val Cys Ser Ser Ser Leu Pro Ala Arg Lys Pro Pro Asn
                165                 170                 175

Glu Pro His Val Tyr Leu Pro Glu Pro Lys Ser Cys Asp Lys Thr His
            180                 185                 190

Thr Cys Pro Pro Cys Pro Ala Pro Glu Leu Leu Gly Gly Pro Ser Val
            195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

```
His Asn His Tyr Thr Gln Lys Ser Leu Ser Leu Ser Pro Gly Lys
                405             410             415
```

<210> SEQ ID NO 42
<211> LENGTH: 193
<212> TYPE: PRT
<213> ORGANISM: Artificial Sequence
<220> FEATURE:
<223> OTHER INFORMATION: cynomolgus monkey RANKL-his

<400> SEQUENCE: 42

```
Met His His His His His His His His His Gly Ser Gln His Ile
1               5                   10                  15

Arg Ala Glu Lys Ala Met Val Asp Gly Ser Trp Leu Asp Leu Ala Lys
                20              25                  30

Arg Ser Lys Leu Glu Ala Gln Pro Phe Ala His Leu Thr Ile Asn Ala
            35                  40                  45

Thr Asp Ile Pro Thr Gly Ser His Lys Val Ser Leu Ser Ser Trp Tyr
        50                  55                  60

His Asp Arg Gly Trp Ala Lys Ile Ser Asn Met Thr Phe Ser Asn Gly
65                  70                  75                  80

Lys Leu Ile Val Asn Gln Asp Gly Phe Tyr Tyr Leu Tyr Ala Asn Ile
                85                  90                  95

Cys Phe Arg His His Glu Thr Ser Gly Asp Leu Ala Thr Glu Tyr Leu
            100                 105                 110

Gln Leu Met Val Tyr Val Thr Lys Thr Ser Ile Lys Ile Pro Ser Ser
            115                 120                 125

His Thr Leu Met Lys Gly Gly Ser Thr Lys Tyr Trp Ser Gly Asn Ser
            130                 135                 140

Glu Phe His Phe Tyr Ser Ile Asn Val Gly Gly Phe Phe Lys Leu Arg
145                 150                 155                 160

Ser Gly Glu Glu Ile Ser Val Glu Val Ser Asn Pro Ser Leu Leu Asp
                165                 170                 175

Pro Asp Gln Asp Ala Thr Tyr Phe Gly Ala Phe Lys Val Arg Asp Ile
                180                 185                 190

Asp
```

<210> SEQ ID NO 43
<211> LENGTH: 193
<212> TYPE: PRT
<213> ORGANISM: Artificial Sequence
<220> FEATURE:
<223> OTHER INFORMATION: Human RANKL-his

<400> SEQUENCE: 43

```
Met His His His His His His His His His Gly Ser Gln His Ile
1               5                   10                  15

Arg Ala Glu Lys Ala Met Val Asp Gly Ser Trp Leu Asp Leu Ala Lys
                20              25                  30

Arg Ser Lys Leu Glu Ala Gln Pro Phe Ala His Leu Thr Ile Asn Ala
            35                  40                  45

Thr Asp Ile Pro Ser Gly Ser His Lys Val Ser Leu Ser Ser Trp Tyr
        50                  55                  60

His Asp Arg Gly Trp Gly Lys Ile Ser Asn Met Thr Phe Ser Asn Gly
65                  70                  75                  80

Lys Leu Ile Val Asn Gln Asp Gly Phe Tyr Tyr Leu Tyr Ala Asn Ile
                85                  90                  95
```

-continued

```
Cys Phe Arg His His Glu Thr Ser Gly Asp Leu Ala Thr Glu Tyr Leu
            100                 105                 110

Gln Leu Met Val Tyr Val Thr Lys Thr Ser Ile Lys Ile Pro Ser Ser
        115                 120                 125

His Thr Leu Met Lys Gly Gly Ser Thr Lys Tyr Trp Ser Gly Asn Ser
    130                 135                 140

Glu Phe His Phe Tyr Ser Ile Asn Val Gly Gly Phe Phe Lys Leu Arg
145                 150                 155                 160

Ser Gly Glu Glu Ile Ser Ile Glu Val Ser Asn Pro Ser Leu Leu Asp
                165                 170                 175

Pro Asp Gln Asp Ala Thr Tyr Phe Gly Ala Phe Lys Val Arg Asp Ile
        180                 185                 190

Asp
```

<210> SEQ ID NO 44
<211> LENGTH: 366
<212> TYPE: DNA
<213> ORGANISM: Artificial Sequence
<220> FEATURE:
<223> OTHER INFORMATION: VH for mouse and chimeric D1A1

<400> SEQUENCE: 44

```
gaggtgcagc tggtggagtc tgggggaggc ttagtgaagt ctggagggtc cctgaaactc    60
tcctgtgcag cctctggatt cactttccgt aactatgcca tgtcttgggt tcgccagact   120
ccggagaaga ggctggagtg ggtcgcagga attagtagtg gtggtactta cacctactat   180
ccagacactg tgaagggacg attcaccatc tccagagaca atgccaggaa caccctgttc   240
ctgcaaatga gcagtctgag gtctgaggac acggccatgt attactgtgc aagaagggac   300
tatggtgatg tctacgaatg gtacttcgat gtctggggca gggaccacg gtcaccgtc    360 tcctca                                                             366
```

<210> SEQ ID NO 45
<211> LENGTH: 321
<212> TYPE: DNA
<213> ORGANISM: Artificial Sequence
<220> FEATURE:
<223> OTHER INFORMATION: VL for mouse and chimeric D1A1

<400> SEQUENCE: 45

```
gacattgtga tgacccagtc tcacaaattc atgtccacat cagtaggaga cagggtcagc    60
atcacctgca aggccagtca ggatgtgaga acttctattg cctggtatca acagaaacca   120
ggacaatctc ctaacctact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcaacaa cattatagtt ctccgtggac gttcggtgga   300
ggcaccaagc tggaaatcaa a                                             321
```

<210> SEQ ID NO 46
<211> LENGTH: 981
<212> TYPE: DNA
<213> ORGANISM: Artificial Sequence
<220> FEATURE:
<223> OTHER INFORMATION: Heavy chain constant region for chimeric
      antibodies

<400> SEQUENCE: 46

```
gcctccacca agggcccatc ggtcttcccc ctggcgccct gctccaggag cacctctgag    60
```

```
agcacagcgg ccctgggctg cctggtcaag gactacttcc ccgaaccggt gacggtgtcg      120
tggaactcag gcgctctgac cagcggcgtg cacaccttcc cagctgtcct acagtcctca      180
ggactctact ccctcagcag cgtggtgacc gtgccctcca gcaacttcgg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaaacccaa ggacaccctc atgatctccc ggacccctga ggtcacgtgc      420
gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac tcccatgct ggactccgac       840 ggctccttct tcctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaatg a                                                981
```

<210> SEQ ID NO 47
<211> LENGTH: 984
<212> TYPE: DNA
<213> ORGANISM: Artificial Sequence
<220> FEATURE:
<223> OTHER INFORMATION: Heavy chain constant region for humanized
      antibodies

<400> SEQUENCE: 47

```
gccagcacaa agggcccttc cgtgtttccc ctggccccct gcagcaggag cacctctgag       60
tccaccgccg ccctgggctg tctggtgaag gactactttc ccgagcccgt gaccgtgagc      120
tggaattccg gcgccctgac atccggcgtg cacaccttcc ccgccgtgct gcagtcctcc      180
ggcctgtaca gcctgagctc cgtggtgaca gtgccttcct cctccctggg caccaagacc      240
tacacatgta atgtggatca caagcccagc aacacaaagg tggataagag agtggagtcc      300
aagtacggcc ctccttgccc ctcctgtcct gccccagagt cctgggcgg ccctctgtg        360 ttcctgttcc cccctaagcc caaggacaca ctgatgatct ccaggacccc tgaggtgacc      420
tgcgtggtgg tggacgtgag ccaggaggac cctgaggtgc agttcaattg gtacgtggat      480
ggcgtggagg tgcacaatgc caagacaaag cccagagagg agcagtttaa ttccacatac      540
agggtggtgt ccgtgctgac cgtgctgcac caggattggc tgaacggcaa ggagtacaag      600
tgtaaggtga gcaacaaggg cctgccttcc tccatcgaga gacaatcag caaggccaag       660 ggccagccta gggagcccca ggtgtacaca ctgcctccca gccaggagga gatgaccaag      720
aaccaggtga gcctgacctg cctggtgaag ggcttctacc ctagcgacat cgccgtggag      780
tgggagtcca acggccagcc cgagaataac tacaagacaa cacccccgt gctggattcc       840 gatggcagct ctttctgta ctccaggctg accgtggata gagcaggtg gcaggagggc        900 aatgtgttca gctgctccgt gatgcacgag gccctgcaca tcactacac ccagaagagc       960 ctgtccctga gcctgggcaa gtga                                             984
```

<210> SEQ ID NO 48

```
<211> LENGTH: 324
<212> TYPE: DNA
<213> ORGANISM: Artificial Sequence
<220> FEATURE:
<223> OTHER INFORMATION: Light chain constant region for chimeric and
      humanized antibodies

<400> SEQUENCE: 48
cgtacggtgg cggcgccatc tgtcttcatc ttcccgccat ctgatgagca gttgaaatct        60
ggaactgcct ctgttgtgtg cctgctgaat aacttctatc ccagagaggc caaagtacag       120
tggaaggtgg ataacgccct ccaatcgggt aactcccagg agagtgtcac agagcaggac       180
agcaaggaca gcacctacag cctcagcagc accctgacgc tgagcaaagc agactacgag       240
aaacacaaag tctacgcctg cgaagtcacc catcagggcc tgagctcgcc cgtcacaaag       300
agcttcaaca ggggagagtg ttga                                             324
```

ANTIBODIES BINDING RANKL AND USES THEREOF

RELATED APPLICATIONS AND INCORPORATION BY REFERENCE

This application claims priority to U.S. provisional application No. 62/947,541 filed on Dec. 13, 2019.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

FIELD OF THE INVENTION

The present disclosure relates generally to an isolated monoclonal antibody, particularly a mouse, chimeric or humanized monoclonal antibody, or an antigen-binding portion thereof, that specifically binds to human RANKL with high affinity and functionality. A nucleic acid molecule encoding the antibody or antigen-binding portion, an expression vector, a host cell and a method for expressing the antibody or antigen-binding portion are also provided. The present disclosure further provides a bispecific molecule and a pharmaceutical composition comprising the antibody or the antigen-binding portion thereof, as well as a diagnostic or treatment method using an anti-RANKL antibody or antigen-binding portion thereof of the disclosure.

BACKGROUND OF THE INVENTION

Receptor activator of nuclear factor kappa-B ligand (RANKL) is a member of tumor necrosis factor (TNF) superfamily, and also known as tumor necrosis factor ligand superfamily member 11 (TNFSF11). It is expressed as a membrane-bound or soluble protein in several tissues and organs, including bone marrow, thymus and lymph nodes, and plays an important role in bone metabolism and immune system development and function (Lacey D. L. et al., (2012) Nat. Rev. Drug Discov. 11(5):401-419; Ahern E. et al., (2018) Nat. Rev. Clin Oncol. 15(11):676-693).

RANKL and its receptor RANK have been implicated in several physiological processes in the immune system. For example, they are necessary for lymph node organogenesis, and regulate T cell development in the thymus. RANKL from activated T cells interacts with RANK on dendritic cells to increase number and persistence of antigen-presenting dendritic cells and antigen-specific T cells, enhancing memory T cell response (Rao S. et al., (2018) Trends Cell Biol. 28(3): 213-223).

RANKL is also a key mediator of pathological bone loss in postmenopausal osteoporosis, multiple myeloma and bone metastases. Upon binding to RANK on myeloid lineage cells, RANKL promotes osteoclast development and contributes to osteoporosis under some conditions such as estrogen loss. RANKL inhibitors have been developed and approved to treat or alleviate such bone destruction. The RANKL's other two receptors, osteoprotegerin (OPG) and LGR4, compete with RANK on RANKL binding and negatively regulate bone resorption (Rao S. et al., cited supra).

One RANKL inhibitor is XGEVA® Denosumab, a fully human IgG2 monoclonal antibody binding RANKL, which has been approved for the treatment of osteoporosis and skeletal-related events (SRE) in cancers. Surprisingly, this antibody showed bone-independent anti-tumor effect in bone metastasis treatment. In a randomized phase III trial with NSCLC patients, those receiving Denosumab had significantly improved overall survival but no significantly superior SRE delay as compared to those administered with bisphosphonate zoledronic acid (Scagliotti G. V. et al., (2012) J. Thorac Oncol., 7 (12): 1823-1829). This anti-tumor effect is probably due to the interruption of RANKL/RANK signalling in the tumor microenvironment (TME) as the interaction of RANKL with RANK expressed by various immune cell types in TME may suppress antitumor immunity (Ahern E. et al., cited supra).

Denosumab has further shown synergic effects with immune checkpoint inhibition in the treatment of tumors, especially those with low baseline RANKL expressions. Immune checkpoint inhibition may result in RANKL upregulation on T cells in TME, and these T cells' anticancer activity may be inhibited following RANKL engagement with RANK expressed on other cells. Concurrent PD-1 and RANKL inhibition, or sequential PD-1 inhibition followed by RANKL inhibition resulted in superior tumor growth suppression in some mouse cancer models (Ahern E. et al., (2018) Oncoimmunology 7(6): e1431088).

Despite of Denosumab's positive benefit-risk profile and good treatment outcomes, adverse effects such as pain, anemia, diarrhea, and skin problems, and in some cases serious infection, have been observed. Therefore, more additional RANKL binding moieties, including antibodies, that are more potent and safe, are needed.

Citation or identification of any document in this application is not an admission that such document is available as prior art to the present disclosure.

SUMMARY OF THE INVENTION

The present disclosure provides an isolated monoclonal antibody, for example, a mouse, human, chimeric or humanized monoclonal antibody, or an antigen-binding portion thereof, that binds to RANKL (e.g., the human RANKL, and monkey RANKL) and has comparable, if not higher, binding affinity/capacity to RANKL and/or blocking capacity on RANK-RANKL interaction as compared to prior art anti-RANKL antibodies such as XGEVA® Denosumab.

The antibody or antigen-binding portion of the disclosure can be used for a variety of applications, including detection of the RANKL proteins, and treatment and prevention of RANKL associated diseases, such as bone loss and cancers.

Accordingly, in one aspect, the disclosure pertains to an isolated monoclonal antibody (e.g., a mouse, chimeric or humanized antibody), or an antigen-binding portion thereof, that binds RANKL, having i) a heavy chain variable region that may comprise a VH-CDR1 region, a VH-CDR2 region and a VH-CDR3 region, wherein the VH-CDR1 region, the VH-CDR2 region and the VH-CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 5 and 10, respectively; (2) SEQ ID NOs: 2, 6 and 11, respectively; (3) SEQ ID NOs: 2, 7 and 11, respectively; (4) SEQ ID NOs: 3, 8 and 12, respectively; or (5) SEQ ID NOs: 4, 9 and 13, respectively; and/or ii) a light chain variable region that may comprise a VL-CDR1 region, a VL-CDR2 region and a VL-CDR3 region, wherein the VL-CDR1 region, the VL-CDR2 region, and the VL-CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 14, 18 and 21, respectively; (2) SEQ ID NOs: 15, 19 and 22, respectively; (3) SEQ ID NOs: 16, 18 and 23, respectively; or (4) SEQ ID NOs: 17, 20 and 24, respectively.

In certain embodiments, the isolated monoclonal antibody, or the antigen-binding portion thereof, of the present disclosure may comprise a heavy chain variable region that may comprise a VH-CDR1 region, a VH-CDR2 region and a VH-CDR3 region, and a light chain variable region that may comprise a VL-CDR1 region, a VL-CDR2 region and a VL-CDR3 region, wherein the VH-CDR1, VH-CDR2, VH-CDR3, VL-CDR1, VL-CDR2 and VL-CDR3 may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 5, 10, 14, 18 and 21, respectively; (2) SEQ ID NOs: 2, 6, 11, 15, 19 and 22, respectively; (3) SEQ ID NOs: 2, 7, 11, 15, 19 and 22, respectively; (4) SEQ ID NOs: 3, 8, 12, 16, 18 and 23, respectively; or (5) SEQ ID NOs: 4, 9, 13, 17, 20 and 24, respectively.

The heavy chain variable region of the antibody or antigen-binding portion of the disclosure may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 25, 26 (X1=A, X2=R, X3=T; X1=S, X2=K, X3=K; or X1=A, X2=K, X3=K), 27 (X1=P, X2=Q; or X1=S, X2=K), 28 or 29. The amino acid sequence set forth in SEQ ID NO: 25 may be encoded by nucleotide sequence of SEQ ID NO: 44.

The light chain variable region of the antibody or antigen-binding portion of the disclosure may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 30, 31 (X1=A, X2=I; or X1=S, X2=L), 32, 33 or 34. The amino acid sequence set forth in SEQ ID NO: 30 may be encoded by nucleotide sequence of SEQ ID NO: 45.

In certain embodiments, the isolated monoclonal antibody, or the antigen-binding portion thereof, of the present disclosure may comprise a heavy chain variable region and a light chain variable region comprising amino acid sequences set forth in (1) SEQ ID NOs: 25 and 30, respectively; (2) SEQ ID NOs: 26 (X1=A, X2=R, X3=T; X1=S, X2=K, X3=K; or X1=A, X2=K, X3=K) and 31 (X1=A, X2=I), respectively; (3) SEQ ID NOs: 26 (X1=A, X2=R, X3=T; X1=S, X2=K, X3=K; or X1=A, X2=K, X3=K) and 31 (X1=S, X2=L), respectively; (4) SEQ ID NOs: 27 (X1=P, X2=Q; or X1=S, X2=K) and 32, respectively; (5) SEQ ID NOs: 28 and 33, respectively, or (6) SEQ ID NOs.: 29 and 34, respectively.

In one embodiment, the isolated monoclonal antibody, or the antigen-binding portion thereof, of the present disclosure may comprise a heavy chain and a light chain, the heavy chain comprising a heavy chain variable region and a heavy chain constant region, the light chain comprising a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above. The heavy chain constant region may be human IgG2 constant region having the amino acid sequence set forth in e.g., SEQ ID No: 35, or human IgG4 constant region having the amino acid sequence set forth in SEQ ID NO.: 36, and the light chain constant region may be human kappa constant region having the amino acid sequences set forth in e.g., SEQ ID No: 37. The amino acid sequences set forth in SEQ ID NOs: 35, 36 and 37 may be encoded by nucleotide sequences of SEQ ID NOs: 46, 47 and 48, respectively.

The antibody of the present disclosure in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to RANKL. The antibody of the disclosure can be a full-length antibody, for example, of an IgG1, IgG2 or IgG4 isotype, or alternatively IgG1 isotype modified to have weak FcR binding capacity and weak/no ADCC/CDC activity. The antibody of the present disclosure in other embodiments may be a single chain variable fragment (scFv) antibody, or antibody fragments, such as Fab or Fab'2 fragments.

The antibody, or antigen-binding portion thereof, of the present disclosure has comparable, if not higher, binding affinity/capacity to human RANKL and monkey RANKL and blocking capacity on RANK-RANKL interaction than prior art anti-RANKL antibodies such as XGEVA® Denosumab.

The disclosure also provides a bispecific molecule comprising an antibody, or antigen-binding portion thereof, of the disclosure, linked to a second functional moiety (e.g., a second antibody) having a different binding specificity than said antibody, or antigen-binding portion thereof.

Nucleic acid molecules encoding the antibodies, or antigen-binding portions thereof, of the disclosure are also encompassed by the disclosure, as well as expression vectors comprising such nucleic acids and host cells comprising such expression vectors. A method for preparing an anti-RANKL antibody or an antigen-binding portion thereof using the host cell comprising the expression vector is also provided, comprising steps of (i) expressing the antibody in the host cell and (ii) isolating the antibody from the host cell or its cell culture.

Compositions comprising the antibody, or antigen-binding portion thereof, the bispecific molecule, the nucleic acid molecule, the expression vector, or the host cell, and a pharmaceutically acceptable carrier, are also provided.

In yet another aspect, the disclosure provides a method for treating a disease associated with increased RANKL expression, comprising administering to a subject a therapeutically effective amount of the antibody, or antigen-binding portion thereof, of the present disclosure. In some embodiments, the method comprises administering a bispecific molecule, a nucleic acid molecule, an expression vector, or a host cell of the disclosure.

The disease may be bone loss or tumor.

The bone loss may be bone destruction in bone metastases, bone loss in multiple myeloma, bone loss in hormone therapy or postmenopausal osteoporosis.

The tumor may be breast cancer, melanoma, prostate carcinoma, colon carcinoma, fibrosarcoma, lung carcinoma, giant cell tumor of bone, multiple myeloma, and/or bone metastases.

In certain embodiments, at least one additional anti-bone loss agent is further administered, such as bisphosphonates, e.g., bisphosphonate zoledronic acid.

In certain embodiments, at least one additional anti-cancer antibody can be further administered, such as an immune checkpoint inhibitor such as an anti-PD-1 antibody, an anti-PD-L1 antibody, an anti-LAG3 antibody, and/or an anti-CTLA-4 antibody. The antibodies of the present disclosure can be, for example, mouse, human, chimeric or humanized antibodies.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

6

Figure 3A:
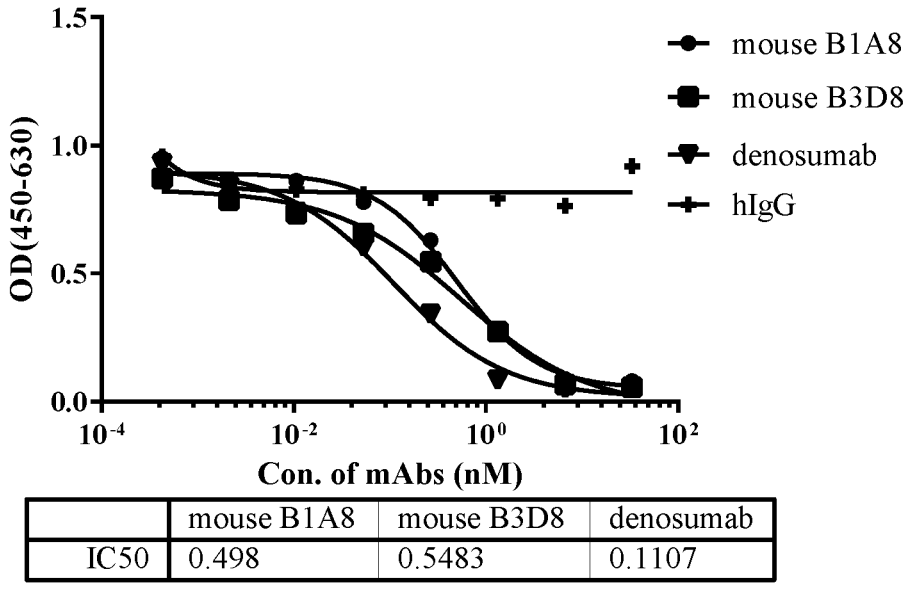
Figure 3B:
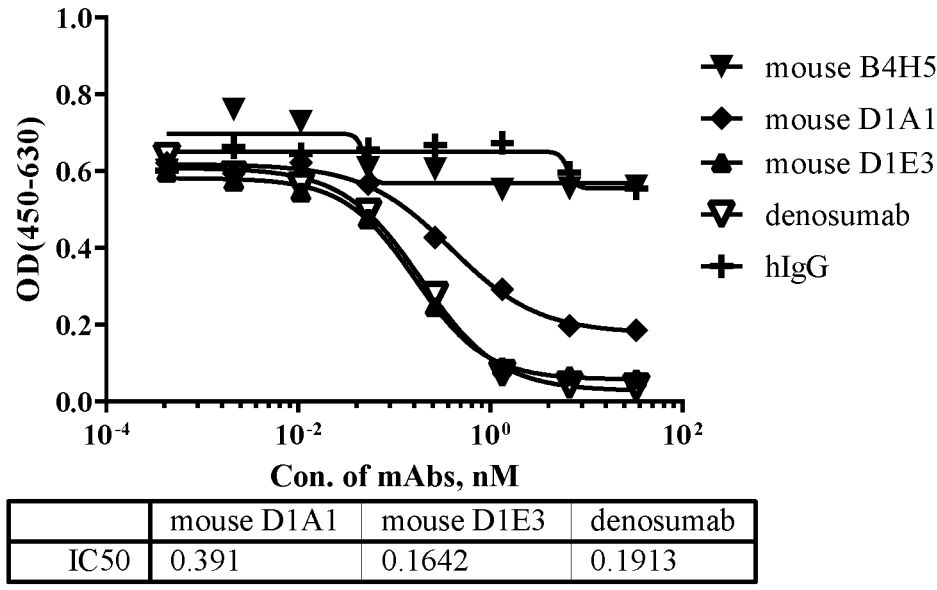

FIGS. 3A and 3B show the abilities of mouse antibodies B1A8 and B3D8 (A), D1E3, D1A1 and B4H5 (B) to block Benchmark-human RANKL binding in a competitive ELISA test.

FIGS. 4A-4D show the abilities of mouse antibodies B1A8 (A), B3D8 and D1A1 (B), D1E3 (C) and B4H5 (D) to block human RANKL binding to cell surface RANK in a cell based functional assay.

FIGS. 5A-5D show the binding capacities of chimeric antibodies B1A8 (A), B3D8 (B), D1E3 (C) and D1A1 (D) to human RANKL in a capture ELISA.

Figure 6:
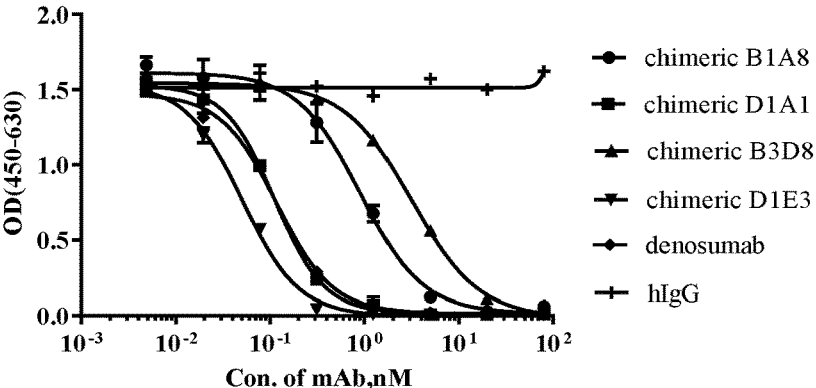

FIG. 6 shows the abilities of chimeric antibodies B1A8, B3D8, D1E3 and D1A1 to block human RANKL-RANK binding in a competitive ELISA.

Figure 7:
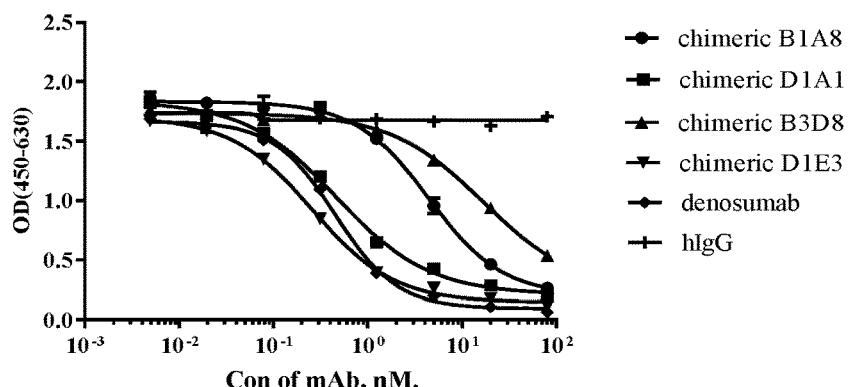

FIG. 7 shows the abilities of chimeric antibodies B1A8, B3D8, D1E3 and D1A1 to block benchmark-human RANKL binding in a competitive ELISA test.

Figure 8:
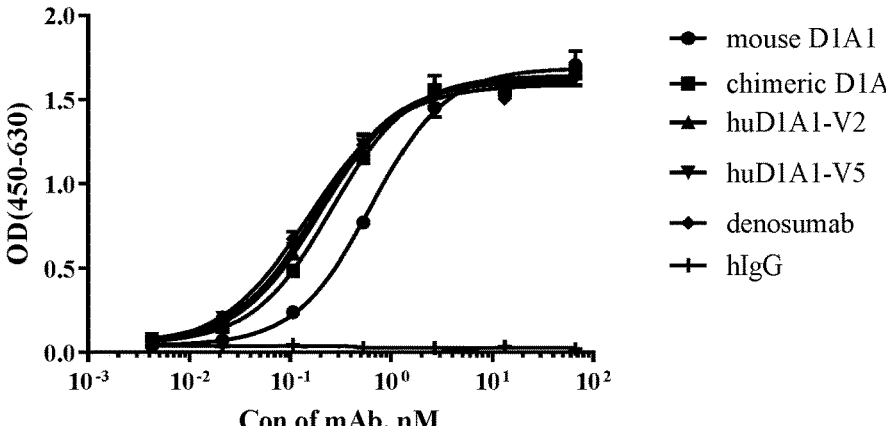

FIG. 8 shows the binding capacities of humanized antibodies huD1A1-V2 and huD1A1-V5 to human RANKL in a capture ELISA.

Figure 9:
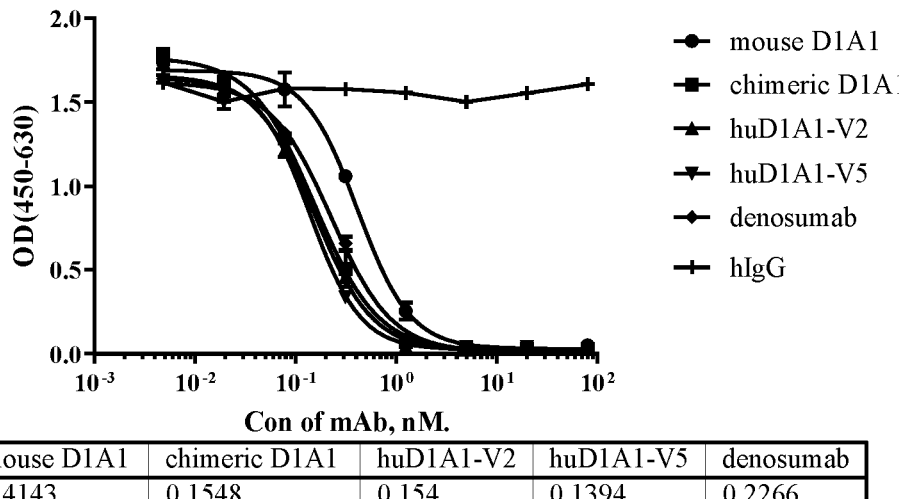

FIG. 9 shows the abilities of humanized antibodies huD1A1-V2 and huD1A1-V5 to block human RANKL-RANK binding in a competitive ELISA.

Figure 10:
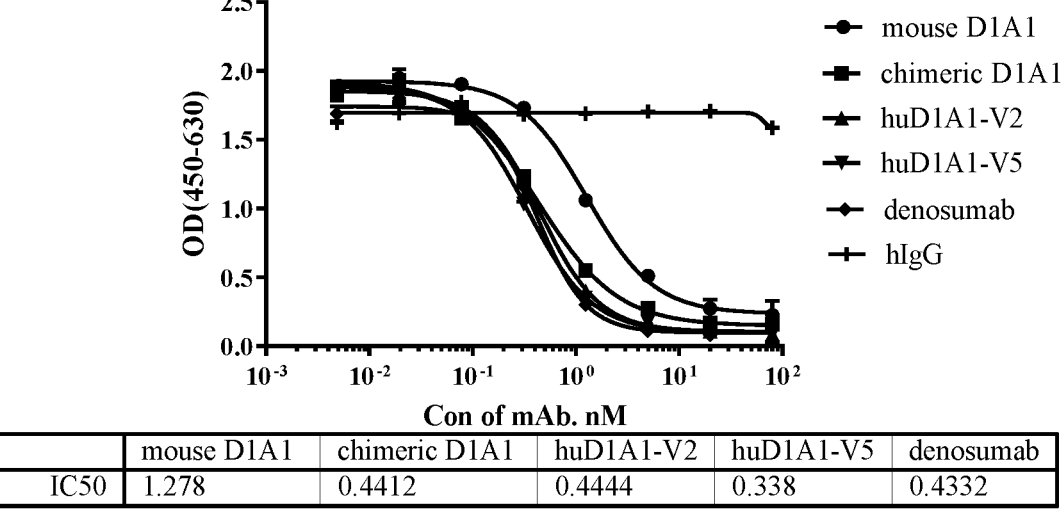

FIG. 10 shows the abilities of humanized antibodies huD1A1-V2 and huD1A1-V5 to block benchmark-human RANKL binding.

Figure 11A:
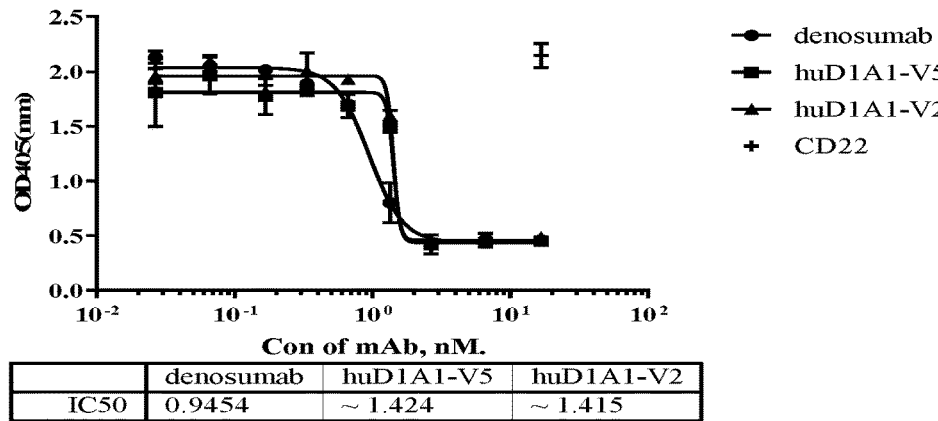
Figure 11B:
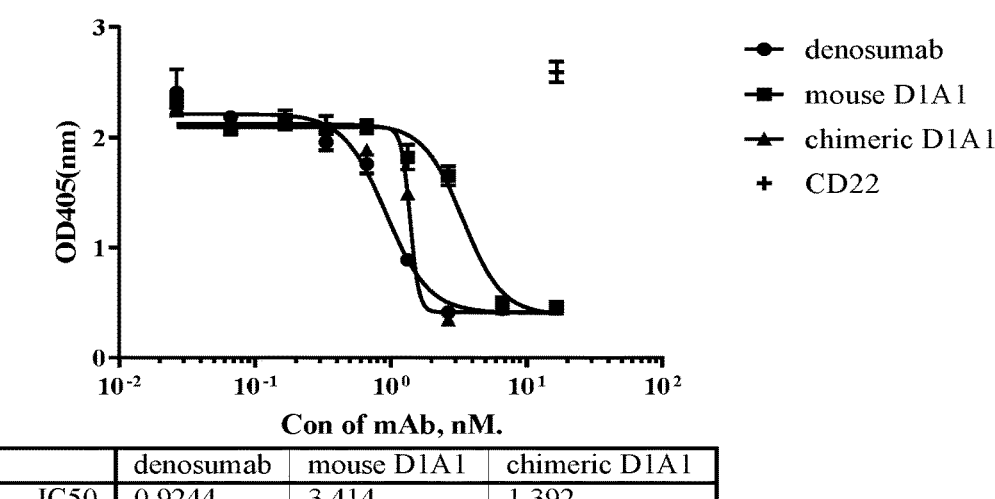
Figure 11C:
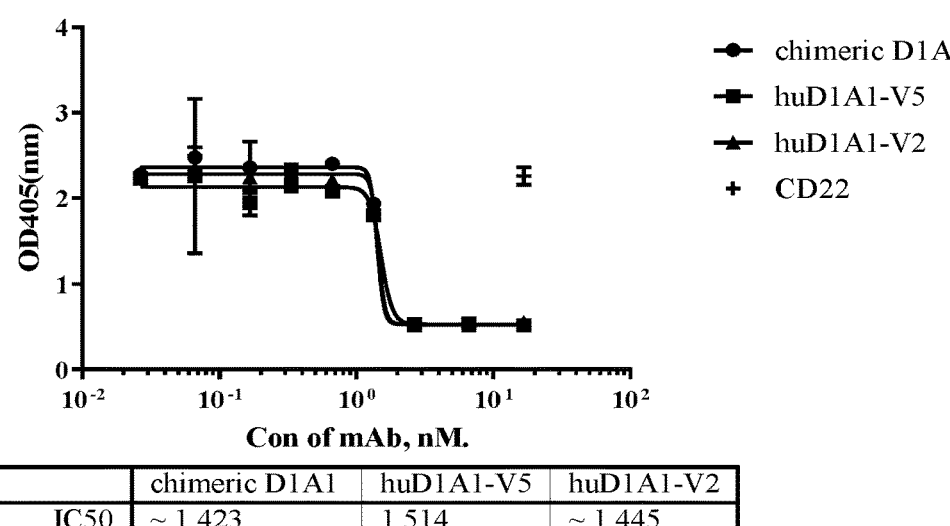

FIGS. 11A-11C show the abilities of humanized antibodies huD1A1-V2 and huD1A1-V5 (A & C) and mouse and chimeric D1A1 antibodies (B) to block human RANKL binding to cell surface RANK in a cell based functional assay.

Figure 12A:
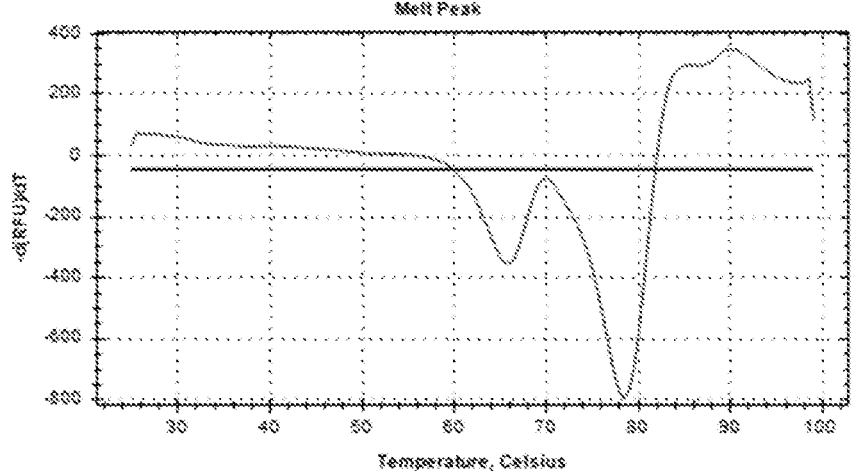
Figure 12B:
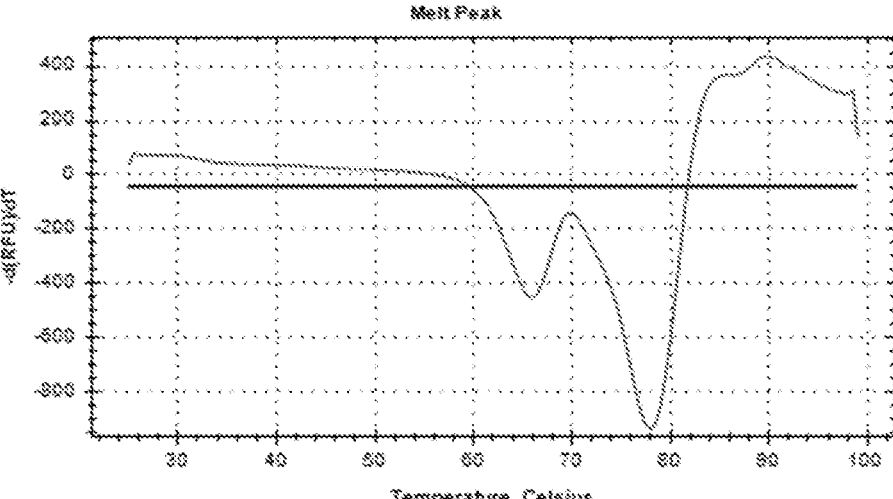

FIGS. 12A-12B show the protein thermal shift assay results of the humanized antibodies hu D1A1-V2 (A) and hu D1A1-V5 (B).

DETAILED DESCRIPTION OF THE INVENTION

To ensure that the present disclosure may be more readily understood, certain terms are first defined. Additional definitions are set forth throughout the detailed description.

The term "RANKL" refers to Receptor activator of nuclear factor kappa-B ligand, or tumor necrosis factor ligand superfamily member 11. The term "RANKL" comprises variants, isoforms, homologs, orthologs and paralogs. For example, an antibody specific for a human RANKL protein may, in certain cases, cross-react with a RANKL protein from a species other than human, such as monkey. In other embodiments, an antibody specific for a human RANKL protein may be completely specific for the human RANKL protein and exhibit no cross-reactivity to other species or of other types, or may cross-react with RANKL from certain other species but not all other species.

The term "human RANKL" refers to a RANKL protein having an amino acid sequence from a human, such as the amino acid sequence of human RANKL having a Genbank accession number of NP_003692.1. The terms "monkey or rhesus RANKL" and "mouse RANKL" refer to monkey and mouse RANKL sequences, respectively, e.g. those with amino acid sequences having Genbank Accession Nos. XP_001092669.1 (*Macaca mulatta*) and NP_035743.2, respectively.

The term "antibody" as used herein refers to an immunoglobulin molecule that recognizes and specifically binds a target, such as RANKL, through at least one antigen-binding site wherein the antigen-binding site is usually within the variable region of the immunoglobulin molecule. As used herein, the term encompasses intact polyclonal antibodies, intact monoclonal antibodies, single-chain Fv (scFv) antibodies, heavy chain antibodies (HCAbs), light chain antibodies (LCAbs), multispecific antibodies, bispecific antibodies, monospecific antibodies, monovalent antibodies, fusion proteins comprising an antigen-binding site of an antibody, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes. Unless expressly indicated otherwise, the term "antibody" as used herein include "antigen-binding portion" of the intact antibodies. An IgG is a glycoprotein which may comprise two heavy (H) chains and two light (L) chains inter-connected by disulfide bonds. Each heavy chain may be comprised of a heavy chain variable region (abbreviated herein as VH) and a heavy chain constant region. The heavy chain constant region may be comprised of three domains, CH1, CH2 and CH3. Each light chain may be comprised of a light chain variable region (abbreviated herein as VL) and a light chain constant region. The light chain constant region may be comprised of one domain, CL. The VH and VL regions can be further subdivided into regions of hypervariability, termed complementarity determining regions (CDR), interspersed with regions that are more conserved, termed framework regions (FR). Each VH and V L is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a RANKL protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment which may comprise two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR); and (viii) a nanobody, a heavy chain variable region containing a single variable domain and two constant domains. Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a RANKL protein is substantially free of antibodies that specifically bind antigens other than RANKL proteins). An isolated antibody that specifically binds a human RANKL protein may, however, have cross-reactivity to other antigens, such as RANKL proteins from other species. Moreover, an isolated antibody can be substantially free of other cellular material and/or chemicals.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human RANKL" is intended to refer to an antibody that binds to human RANKL protein (and possibly a RANKL protein from one or more non-human species) but does not substantially bind to non-RANKL proteins. Preferably, the antibody binds to human RANKL protein with "high affinity", namely with a $K_D$ of $5.0\times10^{-8}$ M or less, more preferably $1.0\times10^{-8}$ M or less, and more preferably $3.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, and even more preferably $3.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as nonhuman primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

Anti-RANKL Antibodies Having Increased Binding Affinity to Human RANKL and Better Blocking Activity on RANKL-RANK Interaction The antibody, or the antigen-binding portion thereof, of the disclosure specifically binds to human RANKL with comparable, if not better, binding affinity/capacity as compared to previously described anti-RANKL antibodies, such as XGEVA® Denosumab.

The antibody, or antigen-binding portion thereof, of the present disclosure has comparable, if not higher, blocking capacity on RANK-RANKL interaction than prior art anti-RANKL antibodies such as XGEVA® Denosumab.

Preferred antibodies of the disclosure are humanized monoclonal antibodies. Additionally or alternatively, the antibodies can be, for example, chimeric monoclonal antibodies.

Monoclonal Anti-RANKL Antibody

The antibody or antigen-binding portion of the disclosure is structurally and chemically characterized below and in the following Examples. The amino acid sequence ID numbers of the heavy/light chain variable regions of the antibodies are summarized in Table 1 below, some antibodies sharing the same $V_H$ or $V_L$. The heavy chain constant region for the antibodies may be human IgG2 heavy chain constant region having an amino acid sequence set forth in, e.g., SEQ ID NO.:35 or human IgG4 heavy chain constant region having an amino acid sequence of SEQ ID NO.:36, and the light chain constant region for the antibodies may be human kappa constant region having an amino acid sequence set forth in, e.g., SEQ ID NO.:37. These antibodies may also contain mouse heavy/light chain constant regions as needed.

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences.

The $V_H$ and $V_L$ sequences (or CDR sequences) of other anti-RANKL antibodies which bind to human RANKL can be "mixed and matched" with the $V_H$ and $V_L$ sequences (or CDR sequences) of the anti-RANKL antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

TABLE 1

| mAb ID | V_H CDR1 | V_H CDR2 | V_H CDR3 | V_H |
|---|---|---|---|---|
| | Amino acid sequence ID numbers of heavy/light chain variable regions and CDRs | | | |
| D1A1 | SEQ ID NO.: 1 | SEQ ID NO.: 5 | SEQ ID NO.: 10 | SEQ ID NO.: 25 |
| huD1A1-V1 | SEQ ID NO.: 1 | SEQ ID NO.: 5 | SEQ ID NO.: 10 | SEQ ID NO.: 26, X1 = A, X2 = R, X3 = T |
| huD1A1-V2 | SEQ ID NO.: 1 | SEQ ID NO.: 5 | SEQ ID NO.: 10 | SEQ ID NO.: 26, X1 = S, X2 = K, X3 = K |
| huD1A1-V3 | SEQ ID NO.: 1 | SEQ ID NO.: 5 | SEQ ID NO.: 10 | SEQ ID NO.: 26, X1 = A, X2 = K, X3 = K |
| huD1A1-V4 | SEQ ID NO.: 1 | SEQ ID NO.: 5 | SEQ ID NO.: 10 | SEQ ID NO.: 26, X1 = A, X2 = R, X3 = T |
| huD1A1-V5 | SEQ ID NO.: 1 | SEQ ID NO.: 5 | SEQ ID NO.: 10 | SEQ ID NO.: 26, X1 = S, X2 = K, X3 = K |
| huD1A1-V6 | SEQ ID NO.: 1 | SEQ ID NO.: 5 | SEQ ID NO.: 10 | SEQ ID NO.: 26, X1 = A, X2 = K, X3 = K |
| B1A8 | SEQ ID NO.: 2 | SEQ ID NO.: 6 | SEQ ID NO.: 11 | SEQ ID NO.: 27, X1 = P, X2 = Q |
| B3D8 | SEQ ID NO.: 2 | SEQ ID NO.: 7 | SEQ ID NO.: 11 | SEQ ID NO.: 27, X1 = S, X2 = K |
| D1E3 | SEQ ID NO.: 3 | SEQ ID NO.: 8 | SEQ ID NO.: 12 | SEQ ID NO.: 28 |
| B4H5 | SEQ ID NO.: 4 | SEQ ID NO.: 9 | SEQ ID NO.: 13 | SEQ ID NO.: 29 |

| mAb ID | V_L CDR1 | V_L CDR2 | V_L CDR3 | V_L |
|---|---|---|---|---|
| D1A1 | SEQ ID NO.: 14 | SEQ ID NO.: 18 | SEQ ID NO.: 21 | SEQ ID NO.: 30 |
| huD1A1-V1 | SEQ ID NO.: 14 | SEQ ID NO.: 18 | SEQ ID NO.: 21 | SEQ ID NO.: 31, X1 = A, X2 = I |
| huD1A1-V2 | SEQ ID NO.: 14 | SEQ ID NO.: 18 | SEQ ID NO.: 21 | SEQ ID NO.: 31, X1 = A, X2 = I |
| huD1A1-V3 | SEQ ID NO.: 14 | SEQ ID NO.: 18 | SEQ ID NO.: 21 | SEQ ID NO.: 31, X1 = A, X2 = I |
| huD1A1-V4 | SEQ ID NO.: 14 | SEQ ID NO.: 18 | SEQ ID NO.: 21 | SEQ ID NO.: 31, X1 = S, X2 = L |
| huD1A1-V5 | SEQ ID NO.: 14 | SEQ ID NO.: 18 | SEQ ID NO.: 21 | SEQ ID NO.: 31, X1 = S, X2 = L |
| huD1A1-V6 | SEQ ID NO.: 14 | SEQ ID NO.: 18 | SEQ ID NO.: 21 | SEQ ID NO.: 31, X1 = S, X2 = L |
| B1A8 | SEQ ID NO.: 15 | SEQ ID NO.: 19 | SEQ ID NO.: 22 | SEQ ID NO.: 32 |
| B3D8 | SEQ ID NO.: 15 | SEQ ID NO.: 19 | SEQ ID NO.: 22 | SEQ ID NO.: 32 |
| D1E3 | SEQ ID NO.: 16 | SEQ ID NO.: 18 | SEQ ID NO.: 23 | SEQ ID NO.: 33 |
| B4H5 | SEQ ID NO.: 17 | SEQ ID NO.: 20 | SEQ ID NO.: 24 | SEQ ID NO.: 34 |

Accordingly, in one embodiment, an antibody of the disclosure, or an antigen binding portion thereof, comprises:

(a) a heavy chain variable region comprising an amino acid sequence listed above in Table 1; and (b) a light chain variable region comprising an amino acid sequence listed above in Table 1, or the V_L of another anti-RANKL antibody, wherein the antibody specifically binds human RANKL.

In another embodiment, an antibody of the disclosure, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-RANKL antibody, wherein the antibody specifically binds human RANKL.

In yet another embodiment, the antibody, or antigen binding portion thereof, includes the heavy chain variable CDR2 region of anti-RANKL antibody combined with CDRs of other antibodies which bind human RANKL, e.g., CDR1 and/or CDR3 from the heavy chain variable region, and/or CDR1, CDR2, and/or CDR3 from the light chain variable region of a different anti-RANKL antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding speci-ficity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIA-journal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-RANKL antibody and at least the CDR3 of the heavy and/or light chain variable region of the anti-RANKL antibody, or the CDR3 of the heavy and/or light chain variable region of another anti-RANKL antibody, wherein the antibody is capable of specifically binding to human RANKL. These antibodies preferably (a) compete for binding with RANKL; (b) retain the functional charac-teristics; (c) bind to the same epitope; and/or (d) have a similar binding affinity as the anti-RANKL antibody of the present disclosure. In yet another embodiment, the antibodies further may comprise the CDR2 of the light chain variable region of the anti-RANKL antibody, or the CDR2 of the light chain variable region of another anti-RANKL antibody, wherein the antibody is capable of specifically binding to human RANKL. In another embodiment, the antibodies of the disclosure may include the CDR1 of the heavy and/or light chain variable region of the anti-RANKL antibody, or the CDR1 of the heavy and/or light chain variable region of another anti-RANKL antibody, wherein the antibody is capable of specifically binding to human RANKL.

Conservative Modifications

In another embodiment, an antibody of the disclosure comprises a heavy and/or light chain variable region sequences of CDR1, CDR2 and CDR3 sequences which differ from those of the anti-RANKL antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof, and/or (b) the heavy chain variable region CDR2 sequence comprises a sequence listed in Table 1 above, and/or conservative modifications thereof, and/or (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human RANKL.

The antibody of the present disclosure possesses one or more of the following functional properties described above, such as high affinity binding to human RANKL, and the ability to induce weak or no ADCC or CDC against RANKL-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered and Modified Antibodies

Antibodies of the disclosure can be prepared using an antibody having one or more of the $V_H/V_L$ sequences of the anti-RANKL antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-RANKL monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha$ (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP, filed on Aug. 11, 2006. PCT Publication WO 99/54342 describes cell lines engineered to express glycoprotein-modifying glycosyl transferases (e.g., $\beta$(1,4)-N-acetylglucaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibody's Physical Properties

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-RANKL antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-RANKL antibody that contains a pI value that falls in the normal range. This can be achieved either by selecting antibodies with a pI in the normal range or by mutating charged surface residues.

Nucleic Acid Molecules Encoding Antibodies of the Disclosure

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the SLAMF7 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Disclosure

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Disclosure

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Bispecific Molecules

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-RANKL binding specificity, a third specificity. The third specificity can be for another immune checkpoint molecules such as PD-1, PD-L1, CTLA-4 or LAG-3.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

Pharmaceutical Compositions

In another aspect, the present disclosure provides a pharmaceutical composition comprising one or more antibodies (or antigen-binding portion thereof, the bispecific molecules, or nucleic acid molecules or expression vectors expressing the same) of the present disclosure formulated together with a pharmaceutically acceptable carrier. The antibodies (or antigen-binding portion thereof, the bispecific molecules, or nucleic acid molecules or expression vectors expressing the same) can be dosed sperapartely when the composition contains more than one antibody (or antigen-binding portion thereof, the bispecific molecule, or nucleic acid molecule or expression vector expressing the same). The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg. An exemplary treatment regime entails administration once per week. Exemplary dosage regimens include intravenous administration.

A "therapeutically effective dosage" of an anti-RANKL antibody, or antigen-binding portion thereof, the bispecific molecules, or nucleic acid molecules or expression vectors expressing the same of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal. For the treatment of bone loss, a "therapeutically effective dosage" preferably inhibits bone loss by at least about 20%, more preferably by at least about 40%, even more preferably by at least about 60%, and still more preferably by at least about 80% relative to untreated subjects.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, poly-orthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies or antigen-binding portion thereof, the bispecific molecules, or nucleic acid molecules or expression vectors expressing the same of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Disclosure

The composition comprising the antibodies or the antigen-binding portion thereof, the bispecific molecules, nucleic acid molecules or expression vectors expressing the same of the present disclosure have numerous in vitro and in vivo utilities involving, for example, treatment of RANKL associated diseases, such as bone loss and cancers.

Given the ability of anti-RANKL antibodies or antigen-binding portion thereof, the bispecific molecules, or nucleic acid molecules or expression vectors expressing the same of the disclosure to inhibit bone destruction, the disclosure provides methods for inhibiting bone loss in a subject comprising administering to the subject the pharmaceutical composition of the disclosure. The bone loss may be bone destruction in bone metastases, multiple myeloma or postmenopausal osteoporosis.

Given the anti-tumor activity of anti-RANKL antibodies or antigen-binding portion thereof, the bispecific molecules, or nucleic acid molecules or expression vectors expressing the same of the disclosure, the disclosure provides methods for inhibiting RANKL related cancers in a subject comprising administering to the subject the pharmaceutical composition of the disclosure such that growth of the tumor is inhibited in the subject. Non-limiting examples of tumors that can be treated by the antibodies or antigen-binding portion thereof, the bispecific molecules, or nucleic acid molecules or expression vectors expressing the same of the disclosure include, but not limited to, breast cancer, melanoma, prostate carcinoma, colon carcinoma, fibrosarcoma, lungcarcinoma, giant cell tumor of bone, multiple myeloma, and bone metastases.

More generally, the antibodies or antigen-binding portion thereof, the bispecific molecules, or nucleic acid molecules or expression vectors expressing the same of the disclosure can be used to enhance an immune response in a subject.

Combination Therapy

In another aspect, the disclosure provides methods of combination therapy in which the anti-RANKL antibodies or antigen-binding portion thereof, the bispecific molecules, or nucleic acid molecules or expression vectors expressing the same of the present disclosure are co-administered with one or more additional agents that are effective in inhibiting bone loss or tumor growth in a subject. The agent for preventing or inhibiting bone loss includes, but not limited to bisphosphonates, such as bisphosphonate zoledronic acid. In certain embodiments, the subject is human.

In one embodiment, the disclosure provides a method for inhibiting tumor growth in a subject comprising administering to the subject an anti-RANKL antibody (or antigen-binding portion thereof, the bispecific molecule, nucleic acid molecule or expression vector expressing the same) and one or more additional antibodies, such as an anti-VISTA antibody, an anti-LAG-3 antibody, an anti-PD-L1 antibody, and anti-PD-1 antibody and/or an anti-CTLA-4 antibody, especially the immune checkpoint inhibitors. In certain embodiments, the subject is human.

The RANKL signaling activation can also be further combined with standard cancer treatments. For example, RANKL signaling activations can be combined with CTLA-4 and/or LAG-3 and/or PD-1 blockade and also chemotherapeutic regimes. For example, a chemotherapeutic agent can be administered with the anti-RANKL antibodies, which may be a cytotoxic agent. For example, epirubicin, oxaliplatin, and 5-FU are administered to patients receiving anti-RANKL therapy.

Optionally, the combination of anti-RANKL and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

Other therapies that may be combined with anti-RANKL antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-RANKL Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. In house made recombinant human RANKL protein (amino acid residue 136-317 of uniport #O14788) with human IgG1 Fc at the C-terminus was used as the immunogen, and also used for determining anti-sera titer and for screening hybridomas secreting antigen-specific antibodies.

Immunizing dosages contained 25 μg human RANKL-Fc protein/mouse/injection for both primary and boost immunizations. To increase immune response, the complete Freud's adjuvant and incomplete Freud's adjuvant (Sigma, St. Louis, Mo., USA) were used respectively for primary and boost immunizations. Briefly, adjuvant-antigen mixture was prepared as follows. First, the adjuvant was mixed in a vial using a vortex. The desired amount of adjuvant was transferred to an autoclaved 1.5 mL micro-centrifuge tube. The antigen was prepared in PBS or saline with concentration ranging from 0.5-1.0 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into the proper syringe for animal injection. A total of 25 μg antigen was injected in a volume of 50-100 μl. Each animal was immunized, and then boosted for 3 to 4 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256: 495-497(1975). Fused "hybrid cells" were subsequently dispensed into 96-well plates in DMEM/20% FCS/HAT medium. Surviving hybridoma colonies were observed under the microscope seven to ten days post fusion. After two weeks, the supernatant from each well was subjected to ELISA-based screening using in house made recombinant human RANKL-Fc protein. Positive hybridomas secreting antibodies that bound to human RANKL-Fc proteins were then selected and transferred to 24-well plates. These hybridomas were further tested for their activities for blocking human RANKL binding to RANK. Hybridoma clones producing antibodies that showed high specific human RANKL binding and RANKL-RANK blocking activities were subcloned by limiting dilution to ensure the clonality of the cell line, and then monoclonal antibodies were purified. Briefly, Protein A sepharose column (from bestchrom (Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C. Subsequently, the in vitro functional activities of purified monoclonal antibodies were characterized as follows.

Example 2 Affinity Determination of Mouse Anti-RANKL Monoclonal Antibodies Using Octet Bio-Layer Interferometry Technology The purified anti-RANKL mouse monoclonal antibodies generated in Example 1 were characterized for affinities and binding kinetics by Octet system (ForteBio, Octet RED 96).

Briefly, AHC/AMC biosensors (anti-human/anti-mouse IgG Fc capture, ForteBio) were presoaked with 10 mM glycine (pH 1.5) for 3 seconds, and then dipped in a well with running buffer (0.5% w/v BSA in PBST) for 3 seconds, the soaking and dipping steps were repeated for three times. Then, the sensors were dipped in a well with anti-RANKL antibodies of the disclosure or a benchmark (denosumab, prepared by using heavy and light chain amino acid sequences of SEQ ID NOs.: 38 and 39, respectively) in HBS-EP$^+$ at 5.0 μg/mL for 100 seconds, and then immersed in a well with in HBS-EP$^+$ for 5 minutes. A new baseline was run for 180 seconds in another well with HBS-EP$^+$. Then the sensors were dipped in a well with serially diluted human RANKL-his protein (prepared in-house with SEQ ID NO: 43, starting at 40 nM with a two-fold serial dilution) in HBS-EP$^+$ for 100 seconds, and then immersed in a baseline well for 10 minutes. Finally, sensors were presoaked with 10 mM glycine (pH 1.5) for 3 seconds, and then dipped in a well with running buffer for 3 seconds, the soaking and dipping steps repeated for three times. The association and dissociation curves were fit to a 1:1 Langmuir binding model using Octet evaluation software. The $K_a$, $K_d$ and $K_D$ values were determined and summarized in Table 2 below.

TABLE 2

| Binding affinity of mouse anti-RANKL antibodies | | | |
| --- | --- | --- | --- |
| | Kinetics on Octet Human RANKL | | |
| Mouse mAb ID# | $K_a$ $(M^{-1}s^{-1})$ | $K_d$ $(s^{-1})$ | $K_D$ (M) |
| D1E3 | not tested | not tested | not tested |
| B3D8 | 6.13E+05 | 2.77E−04 | 4.52E−10 |
| D1A1 | 1.10E+06 | 7.90E−05 | 7.18E−11 |

TABLE 2-continued

| Binding affinity of mouse anti-RANKL antibodies | | | |
| --- | --- | --- | --- |
| | Kinetics on Octet Human RANKL | | |
| Mouse mAb ID# | $K_a$ $(M^{-1}s^{-1})$ | $K_d$ $(s^{-1})$ | $K_D$ $(M)$ |
| B1A8 | 6.11E+05 | 2.36E−04 | 3.86E−10 |
| B4H5 | not tested | not tested | not tested |
| Benchmark | 3.20E+05 | 5.17E−05 | 1.62E−10 |

The mouse anti-RANKL antibodies of the present disclosure, including B3D8, D1A1 and B1A8, specifically bound to human RANKL with comparable binding affinities compared to the benchmark, with D1A1 showing the highest binding affinity.

Example 3 Binding Activity of Mouse Anti-RANKL Monoclonal Antibodies

The binding activities of mouse anti-RANKL antibodies were determined by Capture ELISA.

Briefly, 96-well micro plates were coated with 2.0 μg/ml Affinipure goat anti-mouse IgG F(ab')₂ fragment specific (Jackson Immuno Research, Cat #115-005-072, 100 μl/well) in PBS overnight at 4° C. Plates were washed once with wash buffer (PBS+0.05% v/v Tween-20, PBST) and then blocked with 200 μl/well blocking buffer (5% w/v non-fatty milk in PBST) for 2 hours at 37° C. Plates were washed again and incubated with 100 μl/well serially diluted anti-RANKL antibodies, the benchmark and negative control hIgG (human immunoglobulin (pH4) for intravenous injection, Hualan Biological Engineering Inc.) (5-fold dilution in 2.5% non-fatty milk in PBST, starting with 10000 ng/ml) for 40 minutes at 37° C., and then washed 4 times. Plates containing the captured anti-RANKL antibodies were incubated with biotin-labeled human RANKL-Fc proteins (prepared in house, SEQ ID NO.:40, 22 ng/mL in 2.5% non-fatty milk in PBST, 100 μl/well) for 40 minutes at 37° C., washed 4 times, and incubated with streptavidin conjugated HRP (1:10000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002) at room temperature. The reaction was stopped in 3-10 minutes with 50 μl/well 1M H₂SO₄, and the absorbance of each well was read on a microplate reader using dual wavelengths mode with 450 nm for TMB and 630 nm as the reference wavelength. The OD (450-630) values were plotted against antibody concentration. Data were analyzed using Graphpad Prism software and EC₅₀ values were reported.

Figure 1A:
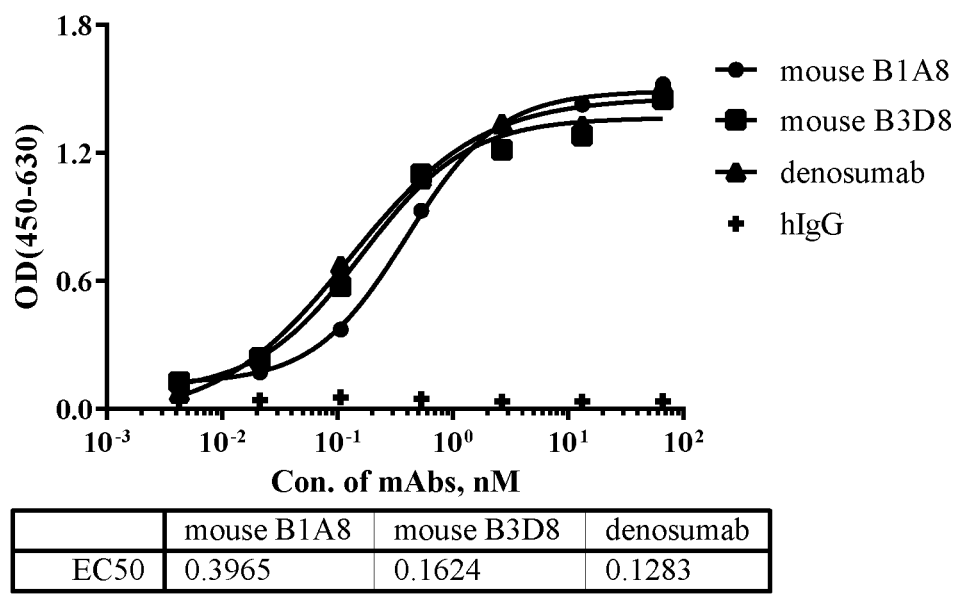
FIGS. 1A and 1B show the binding capacities of mouse antibodies B1A8 and B3D8 (A), D1E3, D1A1 and B4H5 (B) to human RANKL in a capture ELISA.
Figure 1B:
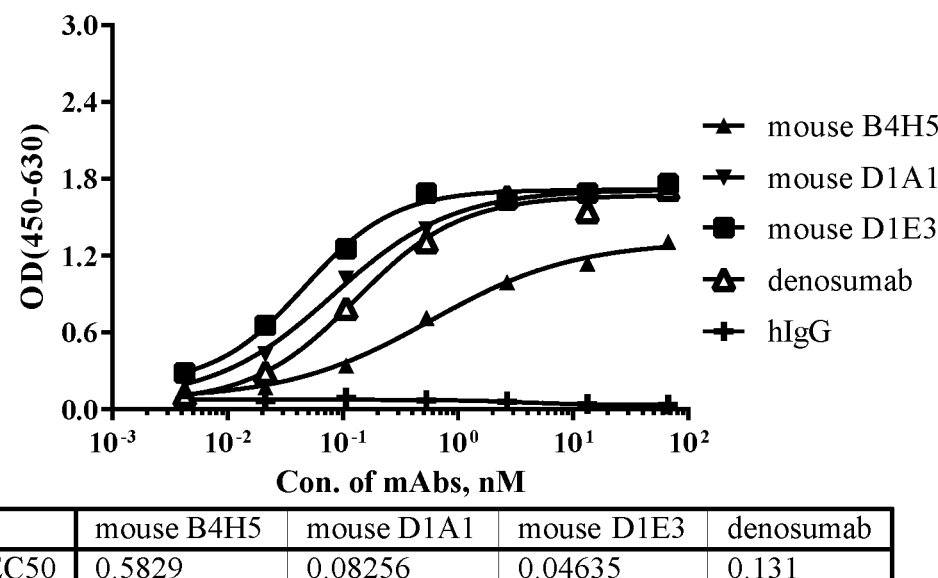

The results were shown in FIGS. 1A and 1B. The results indicated that the mouse anti-RANKL antibodies of the disclosure bound to human RANKL specifically. The maximum absorbance of D1E3/B3D8/D1A1/B1A8/B4H5 was similar to or a bit lower than that of the benchmark, with similar or slightly higher EC₅₀. Especially, the D1E3 and D1A1 antibodies showed lower EC₅₀ values than the benchmark, suggesting that they more efficiently bound to more human RANKL proteins.

Example 4 Competitive ELISA Assays on Mouse Anti-RANKL Antibodies

4.1 Ligand Blocking ELISA

The abilities of anti-RANKL antibodies to block RANKL-RANK binding was measured using a competitive ELISA assay. Briefly, human RANK-Fc proteins (prepared in house, SEQ ID NO.: 41) were coated on 96-well micro plates at 2.0 μg/mL in PBS, 100 μl/well, and incubated overnight at 4° C. The next day, plates were washed with wash buffer (PBS+0.05% w/v Tween-20, PBST), and blocked with 5% w/v non-fatty milk in PBST, 200 μl/well, for 2 hours at 37° C.

The anti-RANKL antibodies of the present disclosure or controls were diluted with biotin labeled human RANKL-Fc protein (prepared in house, SEQ ID NO.: 40, 14.67 ng/mL in 2.5% w/v non-fatty milk in PBST), starting at 20 nM with a 5-fold serial dilution, and incubated at room temperature for 40 minutes. After plate washing, the antibody/RANKL-Fc mixtures were added to the RANK-Fc coated plates, 100 μl/well, and incubated for 40 minutes at 37° C. Plates were washed 4 times using wash buffer, and added and incubated with 100 μl/well of streptavidin conjugated HRP (1:10000 dilution in PBST buffer, Jackson ImmunoResearch Laboratories, Inc., Cat #016-030-084) for 40 minutes at 37° C. Plates were washed again using wash buffer. Finally, TMB was added and the reaction was stopped using 1M H₂SO₄, and the absorbance of each well was read on a microplate reader using dual wavelengths mode with 450 nm for TMB and 630 nm as the reference wavelength. The OD (450-630) values were plotted against antibody concentration. Data were analyzed using Graphpad Prism software and IC₅₀ values were reported.

4.2 Benchmark Blocking ELISA

The abilities of the anti-RANKL antibodies to block Benchmark-human RANKL binding was measured using a competitive ELISA assay. Briefly, the benchmark denosumab was coated on 96-well micro plates at 2 μg/mL in PBS, 100 μl/well, and incubated overnight at 4° C. The next day, plates were washed with wash buffer, and blocked with 5% w/v non-fatty milk in PBST, 200 μl/well, for 2 hours at 37° C. While blocking, the anti-RANKL antibodies of the present disclosure or controls were diluted with biotin labeled human RANKL-Fc protein (SEQ ID NO.: 40, 17.6 ng/mL in 2.5% w/v non-fatty milk in PBST), starting at 80.0 nM with a 4-fold serial dilution, and incubated at room temperature for 40 minutes. After plate washing, the antibody/RANKL-Fc-biotin mixtures were added to the benchmark coated plates, 100 μl/well. After incubation at 37° C. for 40 minutes, plates were washed 4 times using wash buffer. Then the plates were added and incubated with 100 μl Peroxidase Streptavidin (1:5000 dilution in PBST buffer, Jackson Immunoresearch, Cat #016-030-084) for 40 minutes at 37° C. Plates were washed again using wash buffer. Finally, TMB was added and the reaction was stopped using 1M H₂SO₄. The absorbance of each well was read on a microplate reader using dual wavelengths mode with 450 nm for TMB and 630 nm as the reference wavelength, and the OD (450-630) values were plotted against antibody concentration. Data were analyzed using Graphpad Prism software and IC₅₀ values were reported.

The results of the two competition ELISA assays were shown in FIGS. 2A-2B and 3A-3B.

Figure 2A:
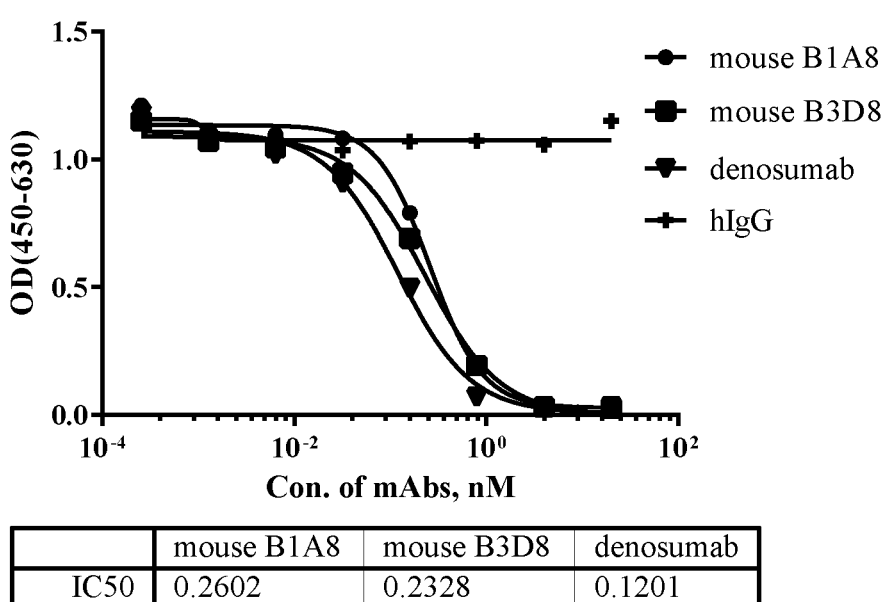
FIGS. 2A and 2B show the abilities of mouse antibodies B1A8 and B3D8 (A), D1E3, D1A1 and B4H5 (B) to block human RANKL-RANK binding in a competitive ELISA.
Figure 2B:
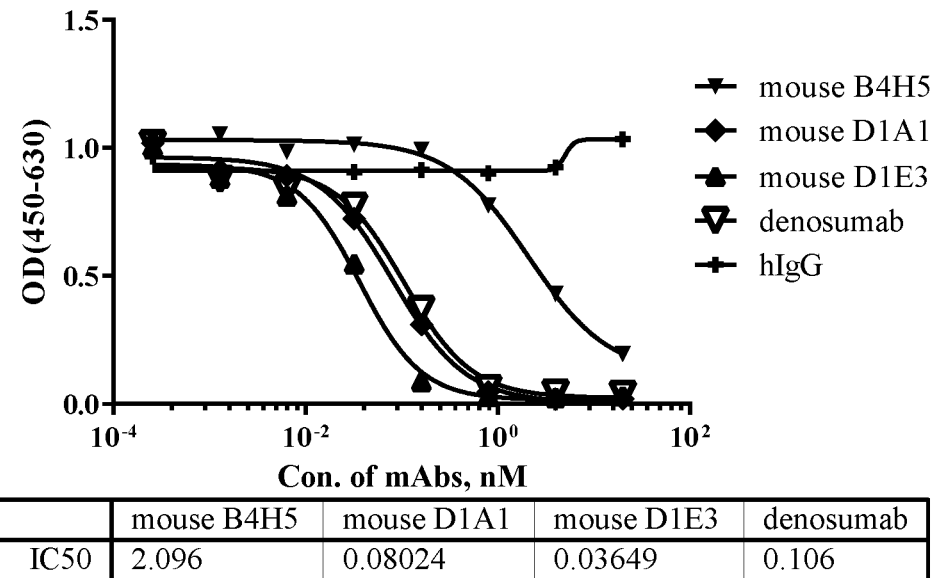

It can be seen from FIGS. 2A-2B that the anti-RANKL antibodies of the disclosure were capable of blocking human RANK-human RANKL interaction. The D1E3 and D1A1 antibodies had lower $IC_{50}$ values as compared to the benchmark, indicating their better blocking activities.

FIGS. 3A and 3B showed that some of the antibodies of the disclosure were able to block human RANKL-benchmark interaction, suggesting that they bound to the same or similar epitope as the benchmark did. The B4H5 antibody showed no blocking activity and may bind to a different epitope.

Example 5 Cell Based Functional Assay of Mouse Anti-RANKL Antibodies

RAW264.7 cells (mouse monocyte-macrophage leukemia cells) may be induced by RANKLs to differentiate into osteoclasts, and such cells may be used to test the anti-RANKL antibodies's capacities of inhibiting RANKL binding to cell surface RANK.

Briefly, RAW 264.7 cells (Cell Bank of Chinese Academy of Sciences, Cat #SCSP-5036) at the log phase were harvested from cell culture flasks, and resuspended in α-MEM medium (Gibco #12561056) supplemented with 10% FBS (Gibco #10091148). $2.0\times10^3$ of RAW 264.7 cells in 150 µl culture medium were plated into 96-well plates, and the plates were incubated in a $CO_2$ incubator at 37° C. for 1 hour. Recombinant human RANKL-his proteins (R&D, Cat #6449-TEC-010) were diluted at 240 ng/ml in α-MEM medium supplemented with 10% FBS. Serially diluted antibodies (final concentration at 16.67 nM, 6.67 nM, 2.67 nM, 1.33 nM, 0.67 nM, 0.33 nM, 0.17 nM, 0.067 nM and 0.0267 nM) in the culture medium prepared above containing RANKL-his protein were added to the plates containing RAW 264.7 cells, 50 µl per well, and incubated in the $CO_2$ incubator at 37° C. for 4 days. After the incubation, the supernatants were removed and the cultured cells in 96-well plates were fixed with 50 µl of ethanol-acetone (50:50, v/v) for 1 min. The plates were centrifuged at 300 g for 3 min and the supernatants were removed gently. Plates were dried at room temperature for 10 min, added with 100 µl pNPP chromogenic solution (Sigma, Cat #S0942-200TAB, for osteoclast staining), and incubated at 37° C. for 30 min. After incubation, the reaction was stopped with 50 µl of 0.5 N NaOH, and absorbance was read at 405 nm. Data were analyzed using Graphpad Prism software and $IC_{50}$ values were reported.

The results of the functional assay were shown in FIGS. 4A-4D.

Figure 4A:
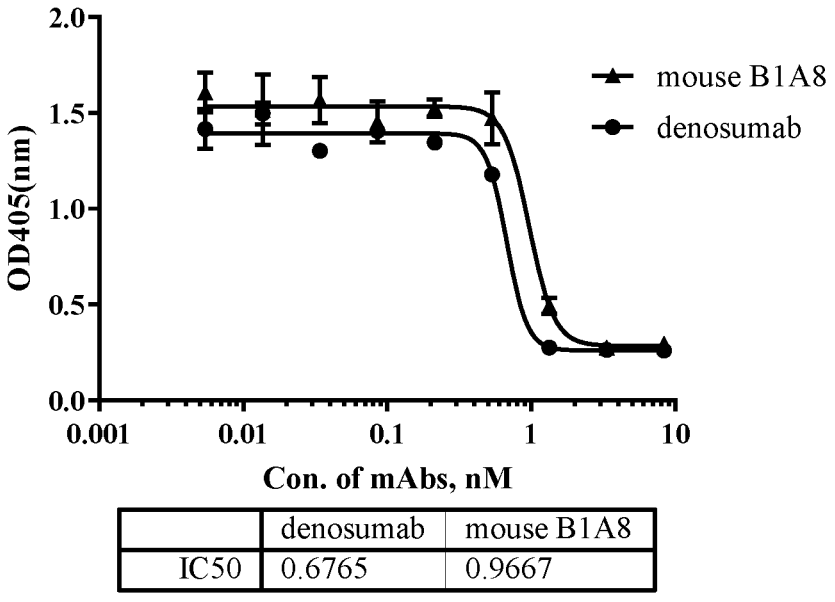
Figure 4B:
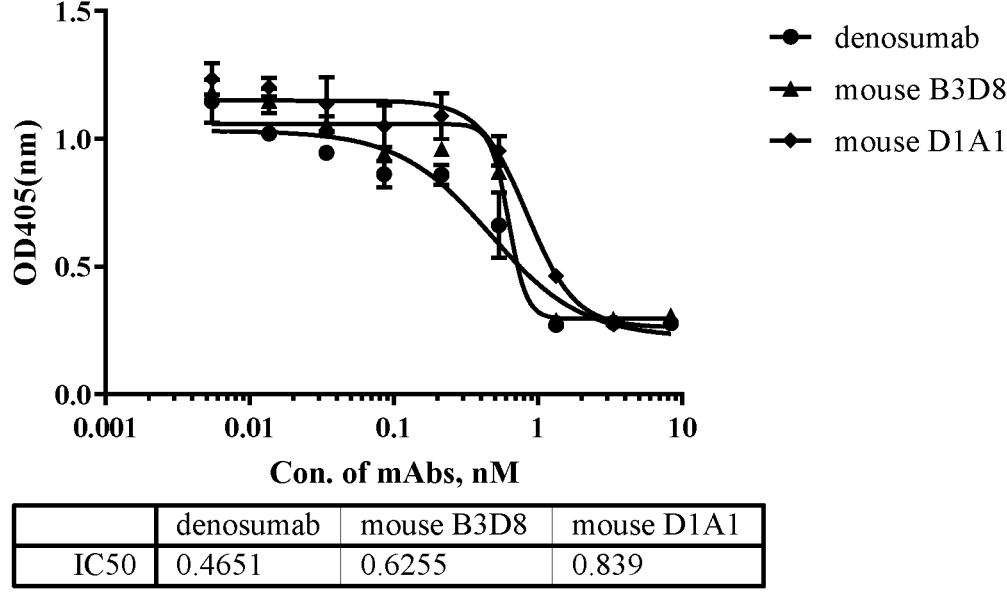
Figure 4C:
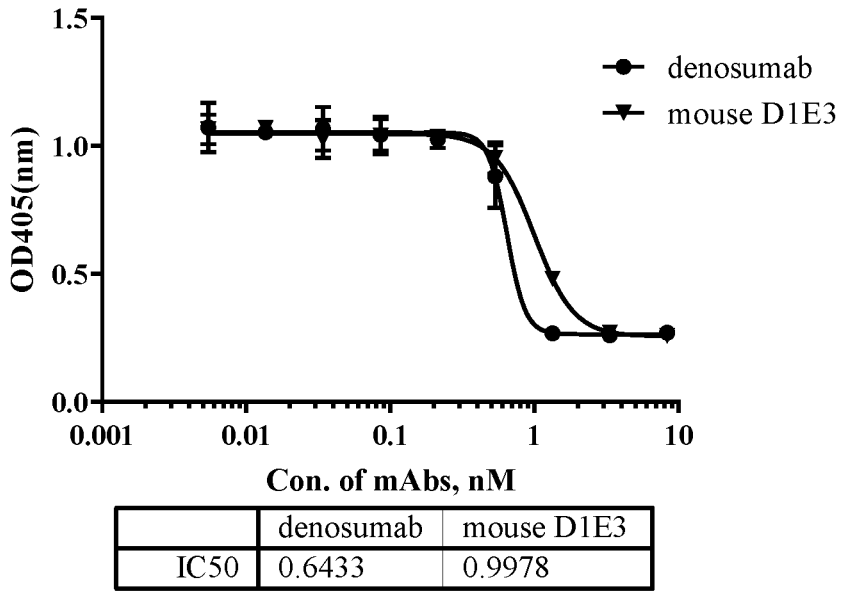
Figure 4D:
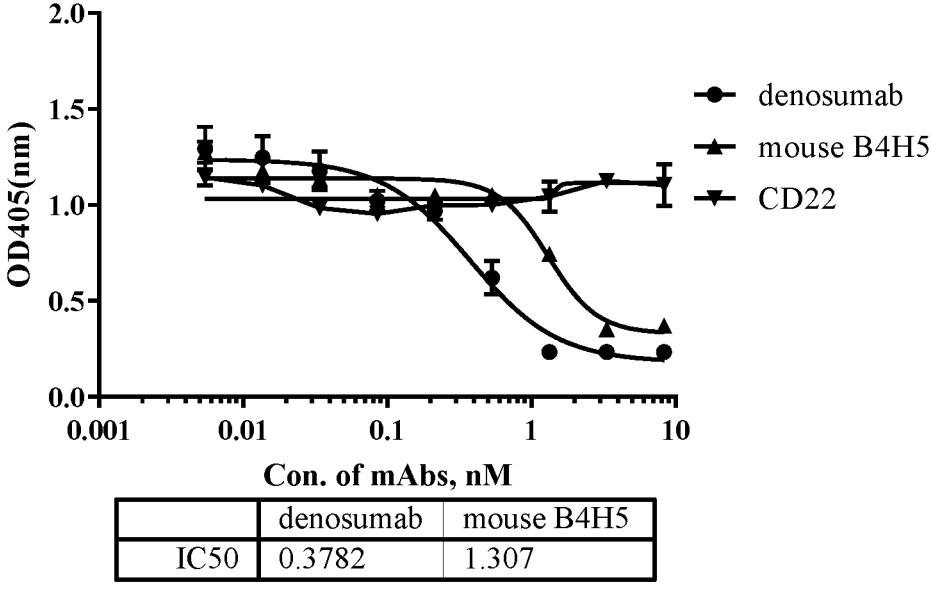
Figure 5A:
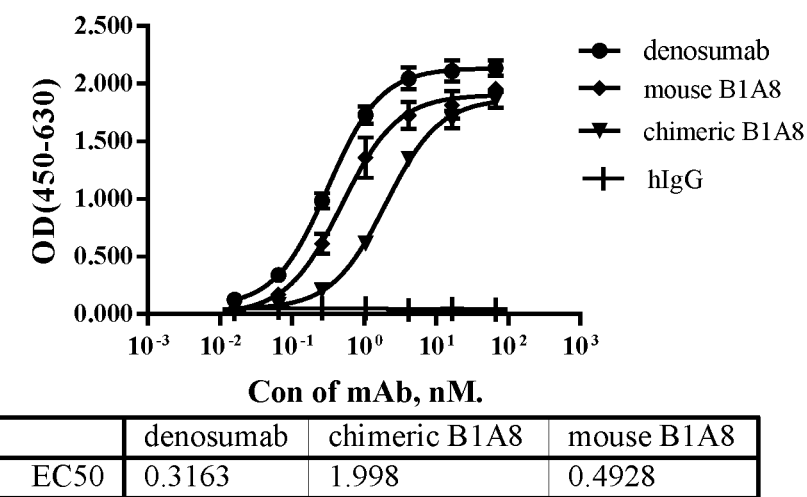
Figure 5B:
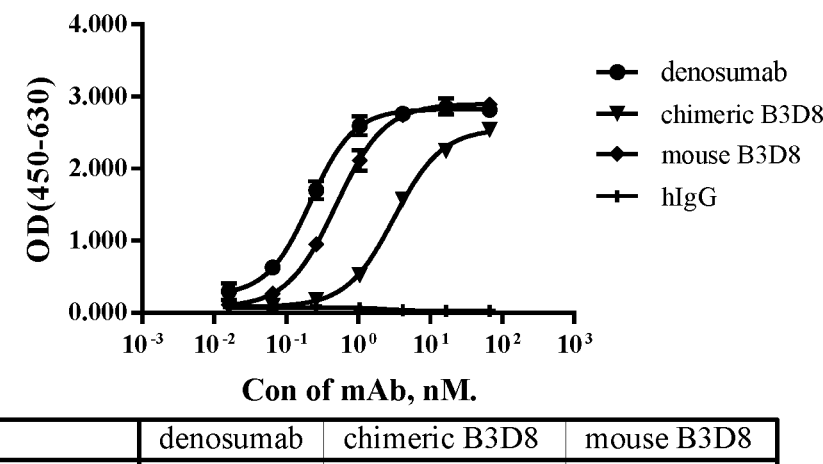
Figure 5C:
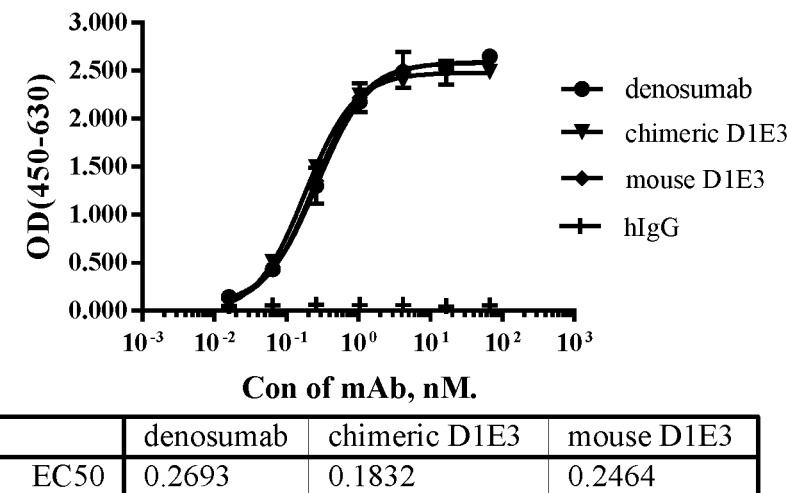
Figure 5D:
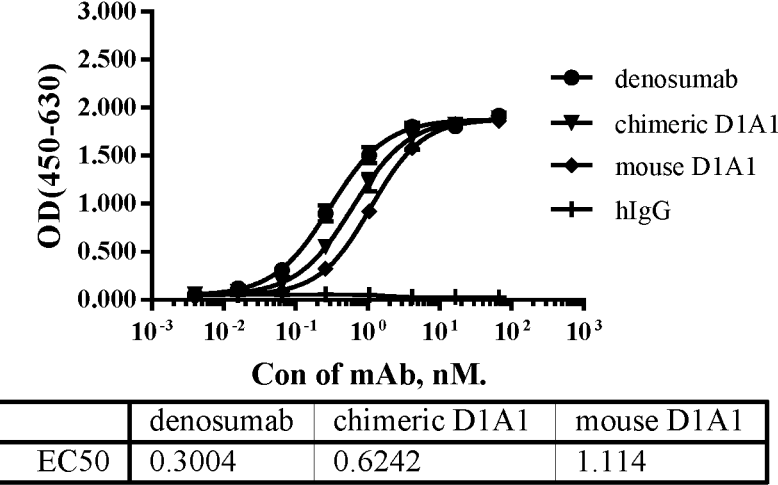

The anti-RANKL antibodies all blocked RANKL binding to cell surface RANK to some extent. FIGS. 4A and 4C showed that the B1A8 and D1E3 had very close blocking capacity to the benchmark, although with a bit higher $EC_{50}$ value.

Example 6 Generation and Characterization of Chimeric Antibodies

The variable domains of the heavy and light chain of the anti-RANKL mouse mAbs were sequenced and the sequence ID numbers were summarized in Table 1.

The variable domains of the heavy and light chain of the anti-RANKL mouse mAbs were cloned in frame to human IgG2 heavy-chain (SEQ ID NO.: 35) and human kappa light-chain constant regions (SEQ ID NO.: 37), respectively, wherein the C terminus of variable region was linked to the N terminus of the respective constant region.

The vectors each containing a nucleotide encoding a heavy chain variable region linked to human IgG2 heavy-chain constant region, and the vectors each containing a nucleotide encoding a light chain variable region linked to human kappa light-chain constant region were transiently transfected into 50 ml of 293F suspension cell cultures in a ratio of 1.1:1 light to heavy chain construct, with 1 mg/mL PEI.

Cell supernatants were harvested after six days in shaking flasks, spun down to pellet cells, and then chimeric antibodies were purified from cell supernatants as described above. The purified antibodies were tested in the capture ELISA, competitive ELISA assay and Octet affinity test following the protocols in the foregoing Examples.

The results were shown in Table 3, FIGS. 5A-5D, 6 and 7.

TABLE 3

| Binding affinities of Chimeric Antibodies | |
|---|---|
| Clone ID# | Octet Affinity to human RANKL (KD, M) |
| Mouse D1E3 | Not tested |
| Chimeric D1E3 | 6.12E−10 |
| Mouse B3D8 | 4.52E−10 |
| Chimeric B3D8 | 2.65E−09 |
| Mouse D1A1 | 7.18E−11 |
| Chimeric D1A1 | 1.97E−10 |
| Mouse B1A8 | 3.86E−10 |
| Chimeric B1A8 | 1.62E−09 |
| Benchmark | 1.62E−10 |

The data showed that the chimeric D1A1 antibody a similar binding affinity/capacity to human RANKL compared to its parental mouse antibody and the benchmark.

Example 7 Humanization of Anti-RANKL Mouse Monoclonal Antibody D1A1

Mouse anti-RANKL antibody D1A1 was selected for humanization and further investigations. Humanization of this mouse antibody was conducted using the well-established CDR-grafting method as described in detail below.

To select acceptor frameworks for humanization of mouse antibody D1A1, the light and heavy chain variable region sequences of mouse D1A1 were blasted against the human immunoglobulin gene database. The human germlines with the highest homology to mouse D1A1 were selected as the acceptor frameworks for humanization. The mouse antibody heavy/light chain variable region CDRs were inserted into the selected frameworks, and the residue(s) in the frameworks was/were further mutated to obtain more candidate heavy chain/light chain variable regions. A total of 6 exemplary humanized D1A1 antibodies (namely from huD1A1-V1 to huD1A1-V6) were obtained whose heavy/light chain variable region sequence number IDs were listed in Table 1.

The vectors each containing a nucleotide sequence encoding the humanized D1A1 heavy chain variable region linked to human IgG4 heavy-chain constant region (SEQ ID NO: 36), and the vectors each containing a nucleotide sequence encoding the humanized D1A1 light chain variable region linked to human kappa light-chain constant region (SEQ ID NO: 37) were transiently transfected into 50 ml of 293F suspension cell cultures in a ratio of 60% to 40% light to heavy chain construct, with 1 mg/ml PEI.

Example 8 Characterization of Humanized D1A1 Antibodies

Cell supernatants containing humanized antibodies were harvested after six days in shaking flasks and tested for binding affinities to human RANKL by Octet affinity test following the protocol described above. The chimeric antibody when tested was in HBS-EP$^+$ at 5 µg/ml concentration. The $K_a$, $K_d$ and $K_D$ values were determined and summarized in Table 4 below.

The results indicated that all humanized D1A1 antibodies had similar human RANKL binding affinities to the chimeric antibody.

TABLE 4

Binding affinities of Humanized D1A1 mAbs
Octet Kinetics of Humanized D1A1 mAbs Binding to Human RANKL

| mAb | Kinetics on Octet Human RANKL his | | |
| | $K_a$ $(M^{-1}s^{-1})$ | $K_d$ $(s^{-1})$ | $K_D$ (M) |
|---|---|---|---|
| huD1A1-V1 | 1.24E+05 | <1.0E−07 | <1.0E−12 |
| huD1A1-V2 | 1.12E+05 | <1.0E−07 | <1.0E−12 |
| huD1A1-V3 | 1.06E+05 | <1.0E−07 | <1.0E−12 |
| huD1A1-V4 | 1.01E+05 | <1.0E−07 | <1.0E−12 |
| huD1A1-V5 | 1.20E+05 | <1.0E−07 | <1.0E−12 |
| huD1A1-V6 | 1.15E+05 | <1.0E−07 | <1.0E−12 |
| Chimeric D1A1 | 1.28E+05 | <1.0E−07 | <1.0E−12 |

The humanized antibodies huD1A1-V2 and huD1A1-V5 were purified as described above and tested for their binding affinities/capacities to human and cynomolgus RANKL and other functional activities by Biacore, binding capture ELISA, protein thermal shift assay, competitive ELISA and cell-based functional assay, following the protocols in the foregoing examples and described below.

The humanized antibodies huD1A1-V2 and huD1A1-V5 were characterized for affinities and binding kinetics by Biacore T200 system (GE healthcare, Pittsburgh, PA, USA) as follows. Briefly, goat anti-human IgG (GE healthcare, Cat #BR100839, Human Antibody Capture Kit) was covalently linked to a CM5 chip (carboxy methyl dextran coated chip from GE healthcare #BR10030) via primary amines, using a standard amine coupling kit provided by Biacore. Unreacted moieties on the biosensor surface were blocked with ethanolamine. Then purified anti-RANKL antibodies at the concentration of 2.0 µg/mL were flown onto the chip at a flow rate of 10 µL/min. Then, recombinant human RANKL-his (prepared in-house with SEQ ID NO: 43) or cynomolgus monkey RANKL-his protein (prepared in-house with SEQ ID NO.:42), 2-fold dilution in HBS-EP$^+$ buffer (provided by Biacore) starting at 80 nM, were flown onto the chip at a flow rate of 30 µL/min. The antigen-antibody association kinetics was followed for 2 minutes and the dissociation kinetics was followed for 10 minutes. The association and dissociation curves were fit to a 1:1 Langmuir binding model using BIAcore evaluation software. The $K_D$ values were determined and summarized in Table 6 below.

To determine the thermal stabilities of humanized antibodies, a protein thermal shift assay was used to determine melting temperature (Tm) using a GloMelt™ Thermal Shift Protein Stability Kit (Biotium, Cat #33022-T). Briefly, the GloMelt™ dye was allowed to thaw and reach room temperature. The vial containing the dye was vortexed and centrifuged. Then, 10× dye was prepared by adding 5 µL 200× dye to 95 µL PBS. 2 µL 10× dye and 10 µg humanized antibodies were added, and PBS was added to a total reaction volume of 20 µL. The tubes containing the dye and antibodies were briefly spun and placed in real-time PCR thermocycler (Roche, LightCycler 480 II) set up with a melt curve program having the parameters in Table 5.

TABLE 5

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

For the capture ELISA, 96-well micro plates were coated with 2 µg/ml goat anti-human IgG (AffiniPure Goat Anti-Human IgG, F(ab')$_2$ fragment specific, Jackson Immunoresearch, Cat #109-005-097) instead of AffiniPure Goat Anti-Mouse IgG, Fcγ fragment specific, 100 µl/well.

The results were shown in Table 6, Table 10, FIGS. 8-10, FIGS. 11A-11C, and FIGS. 12A-12B.

TABLE 6

Binding affinities of Humanized mAbs huD1A1-V2 and huD1A1-V5

| mAbs | Binding assay | | TM (melting temperature), ° C. | |
| | Human RANKL Biacore (KD, M) | Cynomolgus RANKL Biacore (KD, M) | T1 | T2 |
|---|---|---|---|---|
| huD1A1-V2 | 1.34E−10 | 4.2E−10 | 66.0 | 78.5 |
| huD1A1-V5 | 1.79E−10 | 4.14E−10 | 66.0 | 78.0 |
| Chimeric D1A1 | 1.49E−10 | 4.2E−10 | not tested | not tested |
| Mouse D1A1 | not tested | not tested | not tested | not tested |
| Denosumab | 1.2E−10 | 4.61E−10 | not tested | not tested |

The data showed that huD1A1-V2 and huD1A1-V5 showed comparable in vitro activities to chimeric D1A1 antibodies. In particular, chimeric and humanized D1A1 antibodies exhibited high and comparable binding affinities as compared with denosumab in Biacore test, and also showed comparable binding capacities to human RANKL in the ELISA. As shown in FIGS. 9, and 11A-11C, the huD1A1-V2 and huD1A1-V5 blocked binding of human RANKL to RANK at comparable activities to the benchmark.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/ Sequence/SEQ ID NO. |
| --- |

VH CDR1 for mouse, chimeric and humanized D1A1
NYAMS (SEQ ID NO.: 1)

VH CDR2 for mouse, chimeric and humanized D1A1
GISSGGTYTYYPDTVKG (SEQ ID NO.: 5)

VH CDR3 for mouse, chimeric and humanized D1A1
RDYGDVYEWYFDV (SEQ ID NO.: 10)

VL CDR1 for mouse, chimeric and humanized D1A1
KASQDVRTSIA (SEQ ID NO.: 14)

VL CDR2 for mouse, chimeric and humanized D1A1
SASYRYT (SEQ ID NO.: 18)

VL CDR3 for mouse, chimeric and humanized D1A1
QQHYSSPWT (SEQ ID NO.: 21)

VH for mouse and chimeric D1A1
EVQLVESGGGLVKSGGSLKLSCAASGFTFRNYAMSWVRQTPEKRLEWVAGISSGGTYTYYPD
TVKGRFTISRDNARNTLFLQMSSLRSEDTAMYYCARRDYGDVYEWYFDVWGTGTTVTVSS
(SEQ ID NO.: 25)
GAGGTGCAGCTGGTGGAGTCTGGGGGAGGCTTAGTGAAGTCTGGAGGGTCCCTGAAACTC
TCCTGTGCAGCCTCTGGATTCACTTTCCGTAACTATGCCATGTCTTGGGTTCGCCAGACTCC
GGAGAAGAGAGGCTGGAGTGGGTCGCAGGAATTAGTAGTGGTGGTACTTACACCTACTATCC
AGACACTGTGAAGGGACGATTCACCATCTCCAGAGACAATGCCAGGAACACCCTGTTCCTG
CAAATGAGCAGTCTGAGGTCTGAGGACACGGCCATGTATTACTGTGCAAGAAGGGACTAT
GGTGATGTCTACGAATGGTACTTCGATGTCTGGGGCACAGGGACCACGGTCACCGTCTCCT
CA (SEQ ID NO.: 44)

VH for D1A1-V1 and huB1H2-V4
EVQLVESGGGLVKPGGSLRLSCAASGFTFRNYAMSWVRQAPGKGLEWVX1GISSGGTYTYYP
DTVKGRFTISRDNAX2NSLYLQMNSLRAEDTAVYYCARRDYGDVYEWYFDVWGX3GTTVTV
SS (SEQ ID NO.: 26) X1 = A, X2 = R, X3 = T
EVQLVESGGGLVKPGGSLRLSCAASGFTFRNYAMSWVRQAPGKGLEWVAGISSGGTYTYYPD
TVKGRFTISRDNARNSLYLQMNSLRAEDTAVYYCARRDYGDVYEWYFDVWGTGTTVTVSS VH for hu D1A1-V2 and hu D1A1-V5
EVQLVESGGGLVKPGGSLRLSCAASGFTFRNYAMSWVRQAPGKGLEWVX1GISSGGTYTYYP
DTVKGRFTISRDNAX2NSLYLQMNSLRAEDTAVYYCARRDYGDVYEWYFDVWGX3GTTVTV
SS (SEQ ID NO.: 26) X1 = S, X2 = K, X3 = K
EVQLVESGGGLVKPGGSLRLSCAASGFTFRNYAMSWVRQAPGKGLEWVSGISSGGTYTYYPD
TVKGRFTISRDNAKNSLYLQMNSLRAEDTAVYYCARRDYGDVYEWYFDVWGKGTTVTVSS VH for hu D1A1-V3 and hu D1A1-V6
EVQLVESGGGLVKPGGSLRLSCAASGFTFRNYAMSWVRQAPGKGLEWVX1GISSGGTYTYYP
DTVKGRFTISRDNAX2NSLYLQMNSLRAEDTAVYYCARRDYGDVYEWYFDVWGX3GTTVTV
SS (SEQ ID NO.: 26) X1 = A, X2 = K, X3 = K
EVQLVESGGGLVKPGGSLRLSCAASGFTFRNYAMSWVRQAPGKGLEWVAGISSGGTYTYYPD
TVKGRFTISRDNAKNSLYLQMNSLRAEDTAVYYCARRDYGDVYEWYFDVWGKGTTVTVSS VL for mouse and chimeric D11
DIVMTQSHKFMSTSVGDRVSITCKASQDVRTSIAWYQQKPGQSPNLLIYSASYRYTGVPDRFTG
SGSGTDFTFTISSVQAEDLAVYYCQQHYSSPWTFGGGTKLEIK (SEQ ID NO.: 30)
GACATTGTGATGACCCAGTCTCACAAATTCATGTCCACATCAGTAGGAGACAGGGTCAGCA
TCACCTGCAAGGCCAGTCAGGATGTGAGAACTTCTATTGCCTGGTATCAACAGAAACCAGG
ACAATCTCCTAACCTACTGATTTACTCGGCATCCTACCGGTACACTGGAGTCCCTGATCGCT
TCACTGGCAGTGGATCTGGGACGGATTTCACTTTCACCATCAGCAGTGTGCAGGCTGAAGA
CCTGGCAGTTTATTACTGTCAACAACATTATAGTTCTCCGTGGACGTTCGGTGGAGGCACC
AAGCTGGAAATCAAA (SEQ ID NO.: 45)

VL for hu D1A1-V1-hu D1A1-V3
DIQMTQSPSSLSASVGDRVTITCKASQDVRTSIAWYQQKPGKX1PKLLIYSASYRYTGVPSRFSG
SGSGTDFTFTISSLQPEDX2ATYYCQQHYSSPWTFGGGTKVEIK (SEQ ID NO.: 31)
X1 = A, X2 = I
DIQMTQSPSSLSASVGDRVTITCKASQDVRTSIAWYQQKPGKAPKLLIYSASYRYTGVPSRFSGS
GSGTDFTFTISSLQPEDIATYYCQQHYSSPWTFGGGTKVEIK VL for hu D1A1-V4-hu D1A1-V6
DIQMTQSPSSLSASVGDRVTITCKASQDVRTSIAWYQQKPGKX1PKLLIYSASYRYTGVPSRFSG
SGSGTDFTFTISSLQPEDX2ATYYCQQHYSSPWTFGGGTKVEIK (SEQ ID NO.: 31)
X1 = S, X2 = L
DIQMTQSPSSLSASVGDRVTITCKASQDVRTSIAWYQQKPGKSPKLLIYSASYRYTGVPSRFSGS
GSGTDFTFTISSLQPEDLATYYCQQHYSSPWTFGGGTKVEIK

| Description/<br>Sequence/SEQ ID NO. |
| --- |

VH CDR1 for mouse and chimeric B1A8
RYGMS (SEQ ID NO.: 2)

VH CDR2 for mouse and chimeric B1A8
SISSGGTYTSYPDSVQG (SEQ ID NO.: 6)

VH CDR3 for mouse and chimeric B1A8
RNFITSATDCYFDV (SEQ ID NO.: 11)

VL CDR1 for mouse and chimeric B1A8
RASQSISNNLH (SEQ ID NO.: 15)

VL CDR2 for mouse and chimeric B1A8
ASQSIS (SEQ ID NO.: 19)

VL CDR3 for mouse and chimeric B1A8
QQSNSWPFT (SEQ ID NO.: 22)

VH for mouse and chimeric B1A8
EVQLVESGGDLVKX1GGSLKLSCAASGFTFSRYGMSWVRQTPDKRLEWVASISSGGTYTSYPD
SVX2GRFTITRDSAKNTLYLQMSSLKSEDTAMYYCARRNFITSATDCYFDVWGAGTTVTVSS
(SEQ ID NO.: 27) X1 = P, X2 = Q
EVQLVESGGDLVKPGGSLKLSCAASGFTFSRYGMSWVRQTPDKRLEWVASISSGGTYTSYPDS
VQGRFTITRDSAKNTLYLQMSSLKSEDTAMYYCARRNFITSATDCYFDVWGAGTTVTVSS VL for mouse and chimeric B1A8
DTVLTQSPATLSVTPGASVSLSCRASQSISNNLHWYQQKSHESPRLLIIYASQSISGIPSRFSGSGS
GTDFTLSINSVETEDFGVYFCQQSNSWPFTFGGGTKLEIK (SEQ ID NO.: 32)

VH CDR1 for mouse and chimeric B3D8
RYGMS (SEQ ID NO.: 2)

VH CDR2 for mouse and chimeric B3D8
SISSGGTYTSYPDSVKG (SEQ ID NO.: 7)

VH CDR3 for mouse and chimeric B3D8
RNFITSATDCYFDV (SEQ ID NO.: 11)

VL CDR1 for mouse and chimeric B3D8
RASQSISNNLH (SEQ ID NO.: 15)

VL CDR2 for mouse and chimeric B3D8
ASQSIS (SEQ ID NO.: 19)

VL CDR3 for mouse and chimeric B3D8
QQSNSWPFT (SEQ ID NO.: 22)

VH for mouse and chimeric B3D8
EVQLVESGGDLVKX1GGSLKLSCAASGFTFSRYGMSWVRQTPDKRLEWVASISSGGTYTSYPD
SVX2GRFTITRDSAKNTLYLQMSSLKSEDTAMYYCARRNFITSATDCYFDVWGAGTTVTVSS
(SEQ ID NO.: 27) X1 = S, X2 = K
EVQLVESGGDLVKSGGSLKLSCAASGFTFSRYGMSWVRQTPDKRLEWVASISSGGTYTSYPDS
VKGRFTITRDSAKNTLYLQMSSLKSEDTAMYYCARRNFITSATDCYFDVWGAGTTVTVSS VL for mouse and chimeric B3D8
DTVLTQSPATLSVTPGASVSLSCRASQSISNNLHWYQQKSHESPRLLIIYASQSISGIPSRFSGSGS
GTDFTLSINSVETEDFGVYFCQQSNSWPFTFGGGTKLEIK (SEQ ID NO.: 32)

VH CDR1 for mouse and chimeric D1E3
RYAMS (SEQ ID NO.: 3)

VH CDR2 for mouse and chimeric D1E3
GISSGGTYTYYPDTVKG (SEQ ID NO.: 8)

VH CDR3 for mouse and chimeric D1E3
RDYGDVYEWYFDV (SEQ ID NO.: 12)

VL CDR1 for mouse and chimeric D1E3
KASQGVRIAVA (SEQ ID NO.: 16)

VL CDR2 for mouse and chimeric D1E3
SASYRYT (SEQ ID NO.: 18)

-continued

| Description/ |
| Sequence/SEQ ID NO. |

VL CDR3 for mouse and chimeric D1E3
QQHHSSPWT (SEQ ID NO.: 23)

VH for mouse and chimeric D1E3
EVQLVESGGGLVKPGGSLKLSCAASGFTFSRYAMSWVRQTPEKRLEWVAGISSGGTYTYYPDT
VKGRFTISRDSAKNILYLQMGSLRSEDSAMYHCARRDYGDVYEWYFDVWGTGTTVTVSS
(SEQ ID NO.: 28)

VL for mouse and chimeric D1E3
DIVMTQSHKFMSASVGDRVSITCKASQGVRIAVAWYQQKPGQSPKLLIYSASYRYTGVPDRFT
GSGSGTDFTFTISSVQAEDLAVYYCQQHHSSPWTFGGGTKLEIK (SEQ ID NO.: 33)

VH CDR1 for mouse B4H5
SGYSWH (SEQ ID NO.: 4)

VH CDR2 for mouse B4H5
YIHFSGSTNYNPSLKS (SEQ ID NO.: 9)

VH CDR3 for mouse B4H5
SGPSTYVMDY (SEQ ID NO.: 13)

VL CDR1 formouse B4H5
KASQDVGAAVG (SEQ ID NO.: 17)

VL CDR2 for mouse B4H5
WASIRDT (SEQ ID NO.: 20)

VL CDR3 for mouse B4H5
QHYNSYPLT (SEQ ID NO.: 24)

VH for mouse B4H5
DVQLQESGPDLVKPSQSLSLTCTVTGYSISSGYSWHWIRQFPGNKLEWMDYIHFSGSTNYNPSL
KSRISITRDTSKNQFFLQFISVTTEDTATYYCARSGPSTYVMDYWGQGTSVTVSS (SEQ ID
NO.: 29)

VL for mouse B4H5
DIVMTQSHRFMSTSVGDRVSITCKASQDVGAAVGWYQQKPGQSPKLLIYWASIRDTGVPDRFT
GSGSGTDFTLTISNVQSEDLADYFCQHYNSYPLTFGGGTKLEIK (SEQ ID NO.: 34)

Heavy chain constant region for chimeric antibodies
ASTKGPSVFPLAPCSRSTSESTAALGCLVKDYFPEPVTVSWNSGALTSGVHTFPAVLQSSGLYSL
SSVVTVPSSNFGTQTYTCNVDHKPSNTKVDKTVERKCCVECPPCPAPPVAGPSVFLFPPKPKDT
LMISRTPEVTCVVVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQVSLTCLVKGFYPSD
IAVEWESNGQPENNYKTTPPMLDSDGSFFLYSKLTVDKSRWQQGNVFSCSVMHEALHNHYTQ
KSLSLSPGK (SEQ ID NO.: 35)
GCCTCCACCAAGGGCCCATCGGTCTTCCCCCTGGCGCCCTGCTCCAGGAGCACCTCTGAGA
GCACAGCGGCCCTGGGCTGCCTGGTCAAGGACTACTTCCCCGAACCGGTGACGGTGTCGTG
GAACTCAGGCGCTCTGACCAGCGGCGTGCACACCTTCCCAGCTGTCCTACAGTCCTCAGGA
CTCTACTCCCTCAGCAGCGTGGTGACCGTGCCCTCCAGCAACTTCGGCACCCAGACCTACA
CCTGCAACGTAGATCACAAGCCCAGCAACACCAAGGTGGACAAGACAGTTGAGCGCAAAT
GTTGTGTCGAGTGCCCACCGTGCCCAGCACCACCTGTGGCAGGACCGTCAGTCTTCCTCTTC
CCCCCAAAACCCAAGGACACCCTCATGATCTCCCGGACCCCTGAGGTCACGTGCGTGGTGG
TGGACGTGAGCCACGAAGACCCCGAGGTCCAGTTCAACTGGTACGTGGACGGCGTGGAGG
TGCATAATGCCAAGACAAAGCCACGGGAGGAGCAGTTCAACAGCACGTTCCGTGTGGTCA
GCGTCCTCACCGTTGTGCACCAGGACTGGCTGAACGGCAAGGAGTACAAGTGCAAGGTCTC
CAACAAAGGCCTCCCAGCCCCCATCGAGAAAACCATCTCCAAAACCAAAGGGCAGCCCCG
AGAACCACAGGTGTACACCCTGCCCCCATCCCGGGAGGAGATGACCAAGAACCAGGTCAG
CCTGACCTGCCTGGTCAAAGGCTTCTACCCCAGCGACATCGCCGTGGAGTGGGAGAGCAAT
GGGCAGCCGGAGAACAACTACAAGACCACACCTCCCATGCTGGACTCCGACGGCTCCTTCT
TCCTCTACAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTCTCCG
GGTAAATGA (SEQ ID NO.: 46)

Heavy chain constant region for humanized antibodies
ASTKGPSVFPLAPCSRSTSESTAALGCLVKDYFPEPVTVSWNSGALTSGVHTFPAVLQSSGLYSL
SSVVTVPSSSLGTKTYTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQ
KSLSLSLGK (SEQ ID NO.: 36)
GCCAGCACAAAGGGCCCTTCCGTGTTTCCCCTGGCCCCCTGCAGCAGGAGCACCTCTGAGT
CCACCGCCGCCCTGGGCTGTCTGGTGAAGGACTACTTTCCCGAGCCCGTGACCGTGAGCTG
GAATTCCGGCGCCCTGACATCCGGCGTGCACACCTTCCCCGCCGTGCTGCAGTCCTCCGGC
CTGTACAGCCTGAGCTCCGTGGTGACAGTGCCTTCCTCCTCCCTGGGCACCAAGACCTACA -continued

| Description/ |
| --- |
| Sequence/SEQ ID NO. |

CATGTAATGTGGATCACAAGCCCAGCAACACAAAGGTGGATAAGAGAGTGGAGTCCAAGT
ACGGCCCTCCTTGCCCTCCCTGTCCTGCCCCAGAGTTCCTGGGCGGCCCCTCTGTGTTCCTG
TTCCCCCCTAAGCCCAAGGACACACTGATGATCTCCAGGACCCCTGAGGTGACCTGCGTGG
TGGTGGACGTGAGCCAGGAGGACCCTGAGGTGCAGTTCAATTGGTACGTGGATGGCGTGG
AGGTGCACAATGCCAAGACAAAGCCCAGAGAGGAGCAGTTTAATTCCACATACAGGGTGG
TGTCCGTGCTGACCGTGCTGCACCAGGATTGGCTGAACGGCAAGGAGTACAAGTGTAAGGT
GAGCAACAAGGGCCTGCCTTCCTCCATCGAGAAGACAATCAGCAAGGCCAAGGGCCAGCC
TAGGGAGCCCCAGGTGTACACACTGCCTCCCAGCCAGGAGGAGATGACCAAGAACCAGGT
GAGCCTGACCTGCCTGGTGAAGGGCTTCTACCCTAGCGACATCGCCGTGGAGTGGGAGTCC
AACGGCCAGCCCGAGAATAACTACAAGACAACACCCCCCGTGCTGGATTCCGATGGCAGC
TTCTTTCTGTACTCCAGGCTGACCGTGGATAAGAGCAGGTGGCAGGAGGGCAATGTGTTCA
GCTGCTCCGTGATGCACGAGGCCCTGCACAATCACTACACCCAGAAGAGCCTGTCCCTGAG
CCTGGGCAAGTGA (SEQ ID NO.: 47)

Light chain constant region for chimeric and humanized antibodies
RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO.: 37)
CGTACGGTGGCGGCGCCATCTGTCTTCATCTTCCCGCCATCTGATGAGCAGTTGAAATCTGG
AACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGCT
TCAACAGGGGAGAGTGTTGA (SEQ ID NO.: 48)

Heavy chain of denosumab
EVQLLESGGGLVQPGGSLRLSCAASGFTFSSYAMSWVRQAPGKGLEWVSGITGSGGSTYYADS
VKGRFTISRDNSKNTLYLQMNSLRAEDTAVYYCAKDPGTTVIMSWFDPWGQGTLVTVSSAST
KGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYT
QKSLSLSPGK (SEQ ID NO.: 38)

Light chain of denosumab
EIVLTQSPGTLSLSPGERATLSCRASQSVRGRYLAWYQQKPGQAPRLLIYGASSRATGIPDRFSG
SGSGTDFTLTISRLEPEDFAVFYCQQYGSSPRTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKVY
ACEVTHQGLSSPVTKSFNRGEC (SEQ ID NO.: 39)

Human RANKL-Fc
EPKSCDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGKGSQHIRAEKAMVDGSWLDL
AKRSKLEAQPFAHLTINATDIPSGSHKVSLSSWYHDRGWGKISNMTFSNGKLIVNQDGFYYLY
ANICFRHHETSGDLATEYLQLMVYVTKTSIKIPSSHTLMKGGSTKYWSGNSEFHFYSINVGGFF
KLRSGEEISIEVSNPSLLDPDQDATYFGAFKVRDID (SEQ ID NO.: 40)

human RANK-Fc
IAPPCTSEKHYEHLGRCCNKCEPGKYMSSKCTTTSDSVCLPCGPDEYLDSWNEEDKCLLHKVC
DTGKALVAVVAGNSTTPRRCACTAGYHWSQDCECCRRNTECAPGLGAQHPLQLNKDTVCKP
CLAGYFSDAFSSTDKCRPWTNCTFLGKRVEHHGTEKSDAVCSSSLPARKPPNEPHVYLPEPKSC
DKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO.: 41)

cynomolgus monkey RANKL-his
MHHHHHHHHHGSQHIRAEKAMVDGSWLDLAKRSKLEAQPFAHLTINATDIPTGSHKVSLSS
WYHDRGWAKISNMTFSNGKLIVNQDGFYYLYANICFRHHETSGDLATEYLQLMVYVTKTSIKI
PSSHTLMKGGSTKYWSGNSEFHFYSINVGGFFKLRSGEEISVEVSNPSLLDPDQDATYFGAFKV
RDID
(SEQ ID NO.: 42)

Human RANKL-his
MHHHHHHHHHGSQHIRAEKAMVDGSWLDLAKRSKLEAQPFAHLTINATDIPSGSHKVSLSS
WYHDRGWGKISNMTFSNGKLIVNQDGFYYLYANICFRHHETSGDLATEYLQLMVYVTKTSIKI
PSSHTLMKGGSTKYWSGNSEFHFYSINVGGFFKLRSGEEISIEVSNPSLLDPDQDATYFGAFKVR
DID (SEQ ID NO.: 43)

We claim:

1. An antibody, or an antigen-binding portion thereof comprising a heavy chain variable region comprising a VH-CDR1 region, a VH-CDR2 region and a VH-CDR3 region, and a light chain variable region comprising a VL-CDR1 region, a VL-CDR2 region and a VL-CDR3 region, wherein the VH-CDR1 region, the VH-CDR2 region, the VH-CDR3 region, the VL-CDR1 region, the VL-CDR2 region and the VL-CDR3 region comprise amino acid sequences of SEQ ID NOs: 1, 5, 10, 14, 18 and 21, respectively.

2. The antibody, or the antigen-binding portion thereof, of claim 1, wherein the heavy chain variable region comprises an amino acid sequence having at least 85% identity to SEQ ID NOs: 25 or 26, wherein $49^{th}$, $76^{th}$ and $114^{th}$ amino acid residues in SEQ ID NO: 26 are A, R and T respectively; S, K and K respectively; or A, K and K respectively.

3. The antibody, or antigen binding portion thereof, of claim 2, wherein the heavy chain variable region comprises an amino acid sequence having at least 90% identity to SEQ ID NOs: 25 or 26.

4. The antibody, or antigen binding portion thereof, of claim 2, wherein the heavy chain variable region comprises an amino acid sequence having at least 95% identity to SEQ ID NOs: 25 or 26.

5. The antibody, or antigen binding portion thereof, of claim 2, wherein the heavy chain variable region comprises an amino acid sequence having 100% identity to SEQ ID NOs: 25 or 26.

6. The antibody, or the antigen-binding portion thereof, of claim 1, wherein the light chain variable region comprises an amino acid sequence having at least 85% identity to SEQ ID NOs: 30 or 31, wherein $43^{rd}$ and $83^{rd}$ amino acid residues in SEQ ID NO: 31 are A and I respectively; or S and L respectively.

7. The antibody, or antigen binding portion thereof, of claim 6, wherein the light chain variable region comprises an amino acid sequence having at least 90% identity to SEQ ID NOs: 30 or 31.

8. The antibody, or antigen binding portion thereof, of claim 6, wherein the light chain variable region comprises an amino acid sequence having at least 95% identity to SEQ ID NOs: 30 or 31.

9. The antibody, or antigen binding portion thereof, of claim 6, wherein the light chain variable region comprises an amino acid sequence having 100% identity to SEQ ID NOs: 30 or 31.

10. The antibody, or the antigen-binding portion thereof, of claim 2, wherein the heavy chain variable region and the light chain variable region comprise amino acid sequences of (1) SEQ ID NOs: 25 and 30, respectively;

(2) SEQ ID NOs: 26 and 31, respectively, wherein $49^{th}$, $76^{th}$ and $114^{th}$ amino acid residues in SEQ ID NO: 26 are A, R and T respectively; S, K and K respectively; or A, K and K respectively, wherein $43^{rd}$ and $83^{rd}$ amino acid residues in SEQ ID NO: 31 are A and I respectively; or (3) SEQ ID NOs: 26, respectively, wherein $49^{th}$, $76^{th}$ and $114^{th}$ amino acid residues in SEQ ID NO: 26 are A, R and T respectively; S, K and K respectively; or A, K and K respectively, wherein $43^{rd}$ and $83^{rd}$ amino acid residues in SEQ ID NO: 31 are S and L respectively.

11. The antibody, or the antigen-binding portion thereof, of claim 10, comprising a heavy chain constant region having the amino acid sequence of SEQ ID NOs: 35 or 36, linked to the heavy chain variable region, and a light chain constant region having the amino acid sequence of SEQ ID NO: 37, linked to the light chain variable region.

12. The antibody, or antigen binding portion thereof, of claim 1 which binds to Receptor activator of nuclear factor kappa-B ligand (RANKL).

13. The isolated monoclonal antibody, or the antigen-binding portion thereof, of claim 1, which is able to (a) bind human or monkey RANKL; and (b) block RANKL-RANK interaction.

14. The antibody, or the antigen-binding portion thereof, of claim 1, which is a mouse, chimeric or humanized antibody or antigen-binding portion thereof.

15. The antibody, or the antigen-binding portion thereof, of claim 1, which is an IgG1, IgG2 or IgG4 isotype.

16. A pharmaceutical composition comprising a therapeutically effective amount of the antibody, or the antigen-binding portion thereof, of claim 1, and a pharmaceutically acceptable carrier.

17. The pharmaceutical composition of claim 16, further comprising an additional anti-tumor agent or an anti-bone loss agent.

18. A method for treating a disease in a subject, comprising administering to the subject a pharmaceutical composition comprising a therapeutically effective amount of the antibody, or the antigen-binding portion thereof of claim 12 and a pharmaceutically acceptable carrier, wherein the disease is bone loss, breast cancer or prostate carcinoma.

19. The method of claim 8, wherein the bone loss is bone loss in hormone therapy, postmenopausal osteoporosis, bone loss in bone metastasis, or bone loss in multiple myeloma.

\* \* \* \* \*